United States Patent [19]

Peterson et al.

[11] Patent Number: 5,354,268

[45] Date of Patent: Oct. 11, 1994

[54] METHODS AND APPARATUS FOR CONTROL OF VACUUM AND PRESSURE FOR SURGICAL PROCEDURES

[75] Inventors: Erik W. Peterson, Walnut Creek; Donald C. Stenger, Pleasanton, both of Calif.

[73] Assignee: Medical Instrument Development Laboratories, Inc., San Leandro, Calif.

[21] Appl. No.: 971,416

[22] Filed: Nov. 4, 1992

[51] Int. Cl.$^5$ ............................................... A61M 1/00
[52] U.S. Cl. ........................................ 604/35; 604/34; 604/319
[58] Field of Search .................. 128/167, 762; 604/35, 604/48, 65, 118, 119, 131, 132, 133, 317, 319, 320, 321, 322, 323, 324, 325; 215/309

[56] References Cited

U.S. PATENT DOCUMENTS

| | | | |
|---|---|---|---|
| 4,058,123 | 11/1977 | May | 604/35 |
| 4,430,078 | 2/1984 | Sprague | 604/118 |
| 4,475,904 | 10/1984 | Wang . | |
| 4,622,503 | 11/1986 | Sundblom et al. . | |
| 4,627,833 | 12/1986 | Cook | 604/34 |
| 4,706,687 | 11/1987 | Rogers et al. . | |
| 4,713,051 | 12/1987 | Steppe et al. | 604/34 |
| 4,735,610 | 4/1988 | Akkas et al. | 604/319 |
| 4,757,814 | 7/1988 | Wang et al. . | |
| 4,758,220 | 7/1988 | Sundblom et al. . | |
| 4,758,238 | 7/1988 | Sundblom et al. | 604/319 |
| 4,799,924 | 1/1989 | Rosenblatt | 604/118 |
| 4,963,131 | 10/1990 | Wortrich | 604/34 |
| 5,106,366 | 4/1992 | Steppe | 604/34 |
| 5,167,621 | 12/1992 | Band et al. | 604/35 |

OTHER PUBLICATIONS

Instructions for the Installation, Operation and Maintenance, Fairchild Model T6000 Series Miniature Electro-Pneumatic Transducers, General Information, Dec. 1991.

Primary Examiner—John D. Yasko
Assistant Examiner—N. Kent Gring
Attorney, Agent, or Firm—Limbach & Limbach

[57] ABSTRACT

A pneumatic pressure delivery system capable of delivering negative pressure (vacuum or suction) or positive pressure with a precise, continuously variable and predictable control of the pressure delivered is disclosed. The method and apparatus includes the capability of electronically adjusting the variation of pressure to follow any desirable functional mathematical relationship of a control signal. The apparatus includes an electronically controlled pressure regulator in which the pressure at the outlet of a regulator acts upon a piston or diaphragm in opposition to a force produced by an electronic controller. The piston or diaphragm is mechanically coupled to a flow control valve such that the valve alters its position to increase or decrease the flow to its outlet in response to the force exerted on the piston or diaphragm. The invention is also directed toward an aspiration method and apparatus which includes a cassette and a cassette holder to be used in conjunction with the suction and pressure control system. The aspiration method and apparatus utilizes a first chamber having a flexible diaphragm to communicate vacuum to an aspiration port which is connected to a surgical instrument. When the first chamber is nearly filled to capacity, fluid within the first chamber is transferred to a second larger chamber through the application of pressure to the flexible diaphragm. A pair of pinch valves prevents vacuum from being applied to the second chamber and pressure from being applied to the aspiration port.

7 Claims, 21 Drawing Sheets

METHODS AND APPARATUS FOR CONTROL OF VACUUM AND PRESSURE FOR SURGICAL PROCEDURES

BACKGROUND OF THE INVENTION

In the field of surgery, and in particular ophthalmic surgery, it is desirable to provide a system which enables or facilitates the ability of a surgeon to perform a variety of surgical procedures upon an eye. Such procedures include vitrectomy, lens fragmentation, ultrasonic phaco emulsification, and irrigation/aspiration. Such procedures include excising internal tissues of an eye, and may, in certain cases, be followed by what is known as a "fluid-gas exchange". A fluid-gas exchange consists of the infusion of a gas into an eye to express the fluid from the eye to thereby control the intraocular pressure during and after the surgical procedure, as well as to facilitate further surgery within the eye while it is filled with gas.

Accordingly, there is a great need for a suction control system in which the negative pressure level can be very highly controlled. For cutting instruments, such as the vitrectomy probe, which draw tissue into the cutting port by the use of suction, the process of tissue removal is effectively controlled by the level of suction, which is directly related to a negative pressure level. Thus, controlling the negative pressure level to a fine degree is highly desirable to provide the surgeon a concomitant degree of control of the tissue excising process.

In addition, there is also a great need for a pneumatic power delivery system in which the dynamic pressure level applied to an instrument can be highly controlled. One such instrument is a pneumatic scissors handpiece, otherwise termed an intraocular microscissors. For example, when an ophthalmic surgeon is cutting periretinal membrane with a pair of intraocular scissors, one of the blades must be gradually inserted or "teased" under the membrane without damaging the underlying retinal tissue, and the other blade must be closed and opened gradually to prevent irreversible trauma to the retinal tissue.

In order to avoid any irreversible damage to a patient's eye the suction and pressure control system must be precisely responsive to the surgeon✕s control inputs. There remains an intense need for a higher level of performance than has heretofore been achieved, particularly with regard to speed of response and stability of control.

SUMMARY OF THE INVENTION

The present invention is directed toward a pneumatic pressure delivery system capable of delivering either negative pressure (vacuum or suction) or positive pressure with a precise, continuously variable and predictable control of the pressure delivered. The present invention includes the capability of electronically adjusting the variation of pressure to follow any desirable functional mathematical relationship of a control signal. For example, the system may be arranged so that the pressure level will vary linearly with respect to the position of a control lever, pedal or similar adjusting device. Such a system may be utilized for the proportional control of a pneumatic cutting device such as a pneumatic scissors or intraocular microscissors to achieve proportional cutting.

The pressure delivery system of the present invention includes an electronically controlled pressure regulator in which the pressure at the outlet of a regulator acts upon a piston or diaphragm in opposition to a force produced by an electronic controller. A piston or diaphragm is mechanically coupled to a flow control valve such that the valve alters its position to increase the flow to the outlet of a pressure regulator when the force exerted on the piston or diaphragm by the pressure at the output of the regulator is less than the force produced by an electronic control module. Conversely, the valve alters its position to decrease the flow to the outlet of the pressure regulator when the force exerted on the piston or diaphragm by the pressure at the output of the regulator is greater than the force produced by the electronic control module. Thus, the pressure at the outlet tends to remain at a constant level such that the force exerted on the piston or diaphragm balances the force produced by the electronic control means.

In a first preferred implementation of a pressure regulator, the force exerted on the piston or diaphragm is produced by an electromagnetic transducer, such as solenoid which produces a force which is proportional to the electrical current flowing through it. In a second preferred implementation, the force exerted on the piston or diaphragm is produced by fluid pressure. This fluid pressure is regulated by an electronic control module by manipulation of one or more valves.

A further aspect of the present invention is directed toward an aspiration method and apparatus which includes a cassette and fixed control elements to be used in conjunction with said linear suction and pressure control system. The aspiration method and apparatus utilizes the pressure delivery system, together with a venturi vacuum converter to produce a precisely controlled negative pressure which is utilized to aspirate fluid and excised tissue from within an eye. The negative pressure is applied to a flexible diaphragm to create a vacuum within a small volume chamber. By employing a relatively small volume chamber to aspirate such fluids and excised tissue, the response time for desired changes in vacuum (negative pressure) are minimized. When the relatively small volume chamber becomes full, or when otherwise desired, a positive pressure is applied to the flexible bellows to thereby transfer accumulated fluid from the smaller chamber to a larger chamber. The flexible diaphragm, which couples pressure from a gaseous medium to a liquid medium, also isolates the gaseous medium from the liquid medium. The use of such a diaphragm offers several advantages. First, the diaphragm forms a viral barrier between a patient and the aspiration apparatus. Second, the diaphragm produces a viral barrier between successive patients, since the aspiration cassette is intended to be disposed of after each use. Third, the diaphragm prevents bodily fluids from entering the vacuum source of the aspiration apparatus. Fourth, the diaphragm provides quick response to desired changes in suction pressure since there is no flow restricting filter between a vacuum source and a patient.

Yet another aspect of the present invention is directed toward a closed loop pressure control system for gas delivery. In particular, this system utilizes new and improved arrangements for controlling the pressure of a gas which to be delivered into organs such as the eye.

An understanding of the features and advantages of the present invention may be obtained by reference to the detailed description of the invention and the accompanying drawing which set forth illustrative embodiments in which the principles of the invention are utilized.

DETAILED DESCRIPTION OF THE DRAWING

Figure 1:
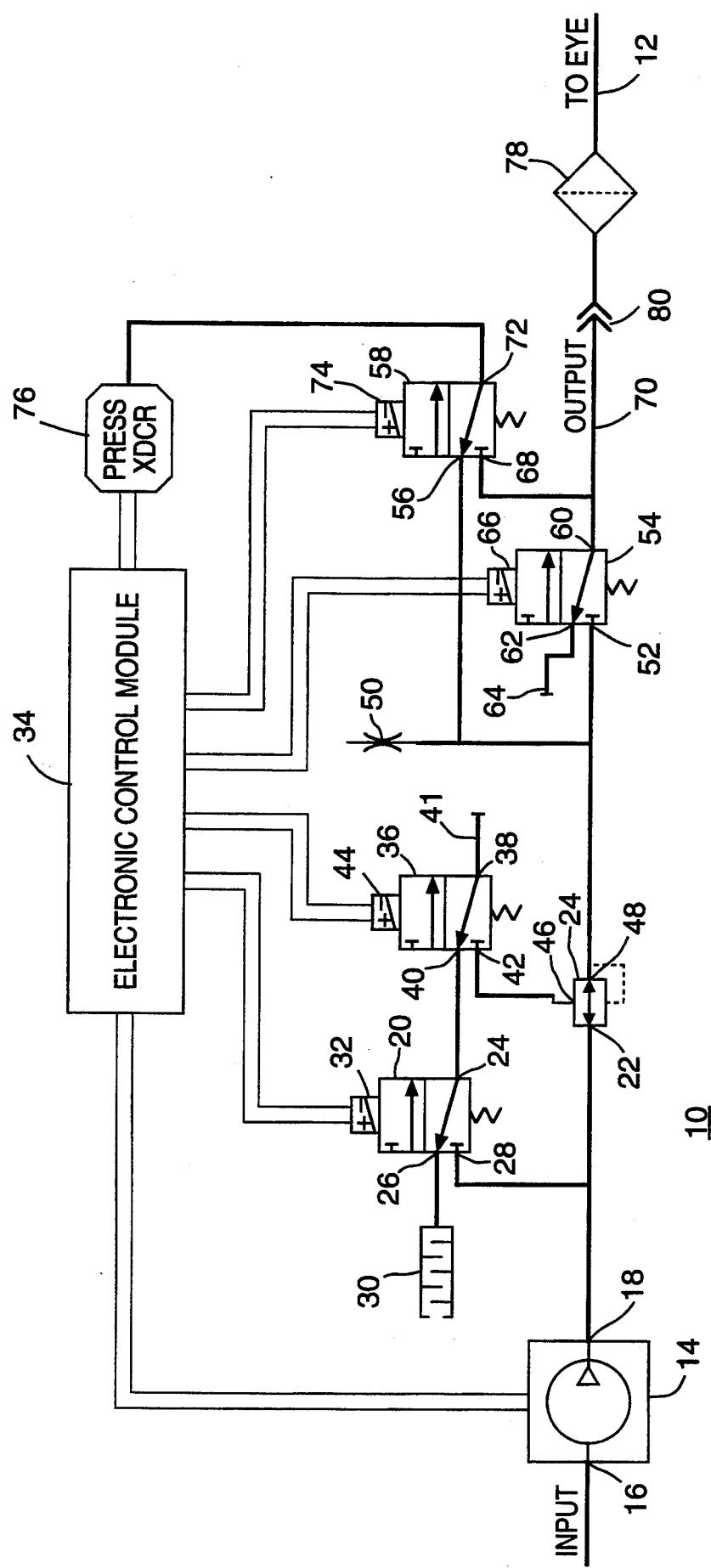
FIG. 1 is a schematic diagram of a first embodiment of a gas delivery system of the present invention.

Referring now to FIG. 1 there is shown a gas delivery system 10 of the present invention. The gas delivery system 10 provides an extremely precise yet adjustable gas pressure to an instrument which is connected to a filtered gas delivery line 12. The system includes a gas pump 14 having an input port 16 and an output port 18. The output port 18 of the pump 14 is connected to both a first three-way valve 20 and a first port 22 of a piloted regulator 24.

The first three-way valve 20 includes a port 24 which is alternately switched between a port 26 and a port 28. The port 26 is connected to a muffler 30. The muffler 30 consists of a centered metal cylinder and functions to reduce the sound pressure level created by changes in pressure at the port 26. The output port 28 of the first three-way valve 24 is also connected to the output port 18 of the pump 14. The first three-way valve 20 also includes a solenoid 32 which is connected to an electronic control module 34.

A second three-way valve 36 includes a port 38 which is alternately switched between a port 40 and a port 42. The port 38 is connected to a plug 41. The port 40 of the second three-way valve 36 is connected to the port 24 of the first three-way valve 20. The second three-way valve 36 also includes a solenoid 44 which is connected to the electronic control module 34. The port 42 of the second three-way valve 36 is connected to a pilot chamber port 46 of the piloted regulator 24. A second port 48 of the piloted regulator 22 is connected to an orifice 50. A port 52 of a third three-way valve 54 is connected to the orifice 50, the port 48 and to a port 56 of a fourth three-way valve 58. The third three-way valve 54 has a port 60 which is alternately switched between the port 52 and a port 62. The port 62 of the three-way valve 54 is connected to a plug 64. The third three-way valve 54 also includes a solenoid 66 which is connected to the electronic control module 34. The port 60 of the third three-way valve 54 is connected to both a port 68 of the fourth three-way valve 58 and to a gas delivery output line 70. A port 72 of the fourth three-way valve 58 is alternately connected between the ports 56 and 68. The fourth three-way valve 58 includes a solenoid 74 which is connected to the electronic control module 34. The port 72 of the fourth three-way valve 58 is pneumatically connected to a pressure transducer 76. The pressure transducer 76 is also connected to the electronic control module 34. The gas delivery output line 70 is coupled to a microbial filter 78 through a coupling 80. The low pressure side of the filter 78 is connected to the filtered gas line 12, which typically is connected to a surgical instrument whose purpose is to deliver controlled pressurized gas within a surgical area.

In operation the gas delivery system 10 operates to deliver air or some other gas into an eye at a precisely controlled pressure over a wide range of flow rates. In conjunction with a suitable aspiration system, such as the one of preferred embodiments described further herein, liquid and excised tissue can be withdrawn from the eye and replaced with gas. The gas filled eye can also be maintained at a constant pressure during subsequent surgical manipulations.

The input port 16 to the pump 14 is normally opened to atmosphere in order to enable the gas delivery system 10 to deliver air. It could however, be connected to a source of some other gas. The pump 14 raises the pressure of the gas to a level greater than the maximum desired output pressure, which is about 2 pounds per square inch (psi). In the event of failure of the pressure regulation mechanism of the system 10, it is desirable that the maximum pressure available from the pump 14 be within a range which can be safely tolerated by the eye for a short period of time. The upper limit of this range is about 5 psi.

With air from the pump 14 flowing through its output port 18 and into the port 22 of the piloted regulator 24, the piloted pressure regulator 24 throttles the flow of air to thereby provide a pressure at its output 48 approximately equal to the pressure applied at the pilot chamber port 46. The pressure at the pilot port 46 is controlled by the first three-way valve 20 and the second three-way valve 36.

To increase the pressure at the pilot port 46, and hence the pressure at the output port 48 of the piloted pressure regulator 24, the first three-way valve 20 is energized in order to connect port 40 through ports 24 and 28 to the output port 18 of the pump 14. The second three-way valve 36 is initially unenergized thereby connecting the internal volume of the second three-way valve 36 to the output port 18 of the pump 14 through the port 40. This internal volume is thus charged to the pressure of the pump 14. The second three-way valve 36 is then energized thereby connecting the internal volume of the second three-way valve 36 to the pilot chamber port 46 of the piloted pressure regulator 24. After a brief period of time the pressure equilibrates at a new value greater than the pressure originally present in the pilot chamber of the piloted pressure regulator 24 and less than the pressure originally present in the internal volume of the second three-way valve 36 (after this internal volume has been charged to the pressure of the pump 14). The exact amount of change depends upon the ratio of the internal volume of the second three-way valve 36 to the volume of the pilot chamber of the piloted pressure regulator 48. Since the former is normally much less than the latter, the pressure change in the pilot chamber of the piloted pressure regulator 24 is a small well-defined fraction of the difference between the pressure initially in the internal volume of the second three-way valve 36 (pump pressure) and the pressure initially in the pilot chamber of the piloted pressure regulator 24. If the pressure in the pilot chamber of the piloted pressure regulator 48 is initially $P_{ppr}$ and the volume of the pilot chamber is $V_{ppr}$, and the pressure within the internal volume [$V_{v2}$] of the second three-way valve 38 is $P_{v2}$, the new pressure will be $P_{ppr}+(P-P_{ppr})$ $(V_{v2}/(V_{v2}+V_{ppr}))$. By making $V_{v2}$ much smaller than $V_{ppr}$, the pressure in the pilot chamber can be adjusted very precisely.

To decrease the pressure at the pilot chamber port 46, and hence the pressure at the output port 48 of the piloted pressure regulator 24, the first three-way valve 20 is unenergized in order to connect the second three-way valve 36 to atmosphere through the muffler 30. The second three-way valve 36 is initially unenergized, thereby connecting the internal volume of the second three-way valve 36 to atmospheric pressure. The pressure of this internal volume equilibrates to atmospheric pressure. The second three-way valve 36 is then energized, thereby connecting the internal volume of the second three-way valve 36 to the pilot chamber through the pilot chamber port 46 of the piloted pressure regulator 24. After a brief period of time, the pressure equilibrates at a new value less than the pressure originally present in the pilot chamber of the piloted pressure regulator 24 and greater than the pressure originally present in the atmospheric pressure internal volume of the second three-way valve 36.

After a period of time sufficient for equilibration of pressures, the second three-way valve 36 is returned to unenergized state. The system 10 is then ready to begin another cycle, if needed to further adjust the pressure applied to the pilot port 46 and thus to the pilot chamber of the piloted pressure regulator 24.

A brief period of time is allowed for equilibration of the output pressure at port 48 of the piloted pressure regulator 24. The pressure measured by the pressure transducer 76 is then compared with the desired pressure as determined and set by the surgeon through the electronic control module 34. If the actual pressure is less than the desired pressure by more than an allowed tolerance, the first three-way valve 20 and the second three-way valve 36 are operated through another cycle so as to increase the pressure at the pilot chamber port 46 of the piloted pressure regulator 24. If the actual pressure is greater than the desired pressure by more than the allowed tolerance, the first three-way valve 20 and the second three-way valve 36 are operated through another cycle so as to decrease the pressure at the pilot chamber port 46 of the piloted pressure regulator 48. If the actual pressure is within the allowed tolerance of the desired pressure, the first and second three-way valves 20 and 36 are not cycled and the pressure comparison through the pressure transducer 76 is repeated on a periodic basis.

The third three-way valve 54 serves to block flow of the output line 70. This blocking can be useful when testing the operation of the system 10 prior to establishing a connection to an eye. The third three-way valve 54 can also prevent back flow from the eye into the system 10, in the unlikely event that a failure prevents the system 10 from maintaining pressure at the output line 70.

In particular, the third three-way valve 36 is arranged to block flow when the system 10 is unenergized. Thus a loss of electrical power to the system 10 does not result in fluid flow from the eye to the system 10.

The fourth three-way valve 58 connects the pressure transducer 76 to one of the two alternate ports 56 or 68 for the pressure measurement. In normal operation, the fourth three-way valve 58 is energized so that the site of measurement is as close to the output of the system 10 as is practical. This insures that the pressure drop across the third three-way valve 54 at high flow rates does not result in a decreased pressure at the output line 70. In certain circumstances, however, the third three-way valve 54 may be unenergized, thereby blocking flow from the piloted regulator valve 24 to the output line 70. The fourth three-way valve 58 must then be also unenergized, thereby connecting the pressure transducer 76 to a site where the pressure can continue to be controlled by the electronic control module 34. If this were not done, the control loop of the system 10 would be broken, and the output of the piloted pressure regulator 24 could be driven to a very high or very low pressure. Thus, a hazardous situation could exist at the time that the third three-way valve 54 is once again energized connecting this high or low pressure to the eye.

The orifice 50 improves regulation by ensuring that there is always some flow through the piloted pressure regulator 24. Without such flow, it might not be possible to decrease the pressure at the output line 70, since flow through the piloted regulator 24 is always from the pump 14 toward the output line 70, and to decrease pressure within any given volume (assuming a relatively constant temperature), gas must be released.

Figure 2:
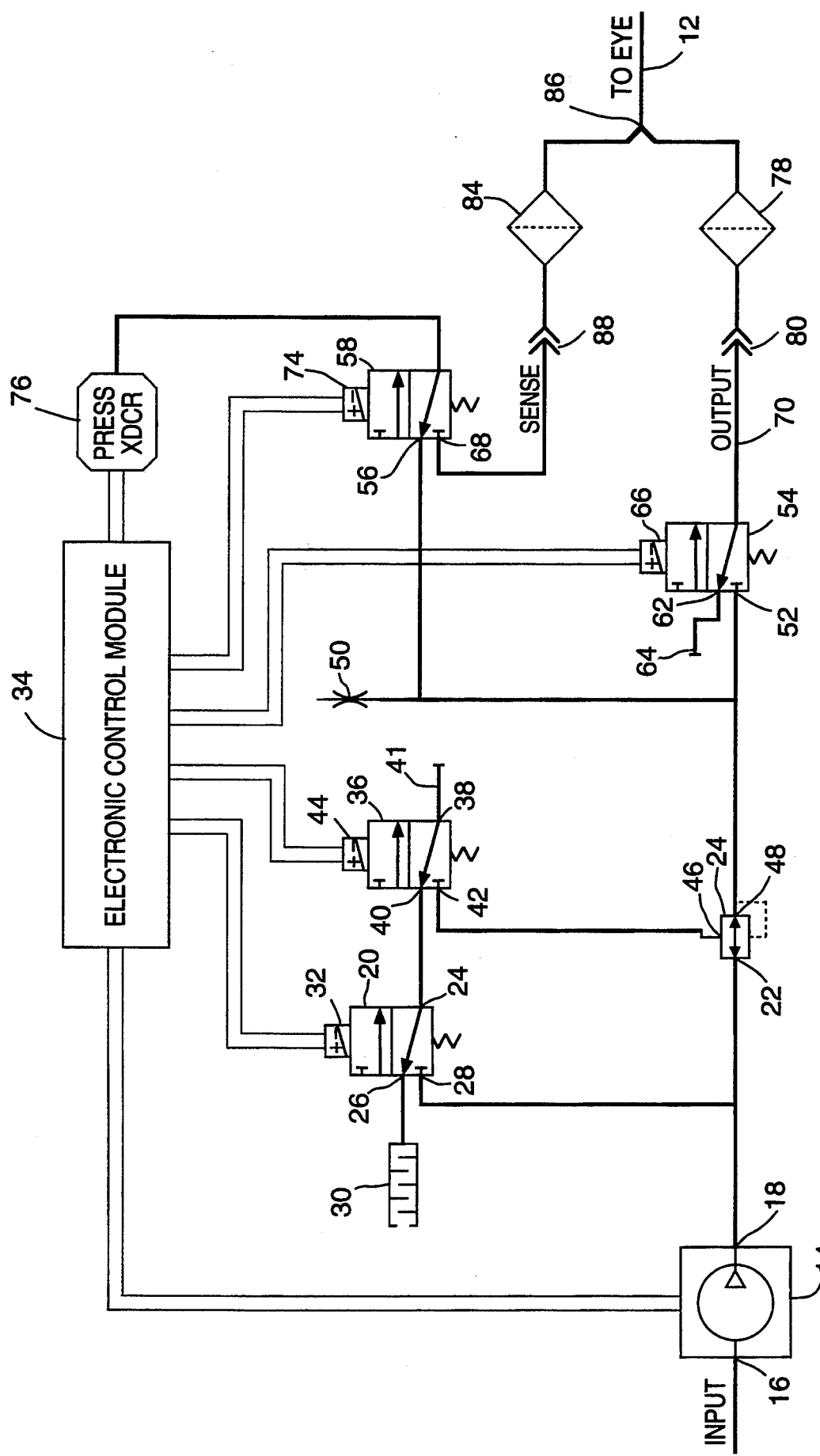
FIG. 2 is a schematic diagram of a second embodiment of a gas delivery system of the present invention.

The disposable portion of the system 10 normally incorporates the filter 78 to remove bacterial contamination from gas before it enters the eye. At high flow rates, the pressure drop across the filter 78 can cause the pressure delivered to the eye to be significantly reduced. Referring now to both FIGS. 1 and 2 the disposable portion of the system 10 consists of the filter 78 its associated portion of the coupling 80. An alternative embodiment of the system 10 is shown in FIG. 2. A gas delivery system 82 shown in FIG. 2 includes a second filter 84 as part of the disposable portion of the system 82. The disposable filter 84 is coupled to the filtered gas delivery line 12 through a junction 86. The other side of the filter 84 is connected to the port 68 of the three-way valve 58 through a coupling 88. In this arrangement the pressure sensor 76 senses the pressure downstream of the filter 78 to thereby enable the system 82 to compensate for the pressure drop across the filter 78. The filter 84 is required to protect the eye from bacterial contamination which could otherwise enter the filtered gas delivery line 12 through or from the fourth three-way valve 58. The filter 84 does not introduce any significant error into the measurement of pressure by the transducer 76 because there is no steady state flow through the filter 84.

Figure 3:
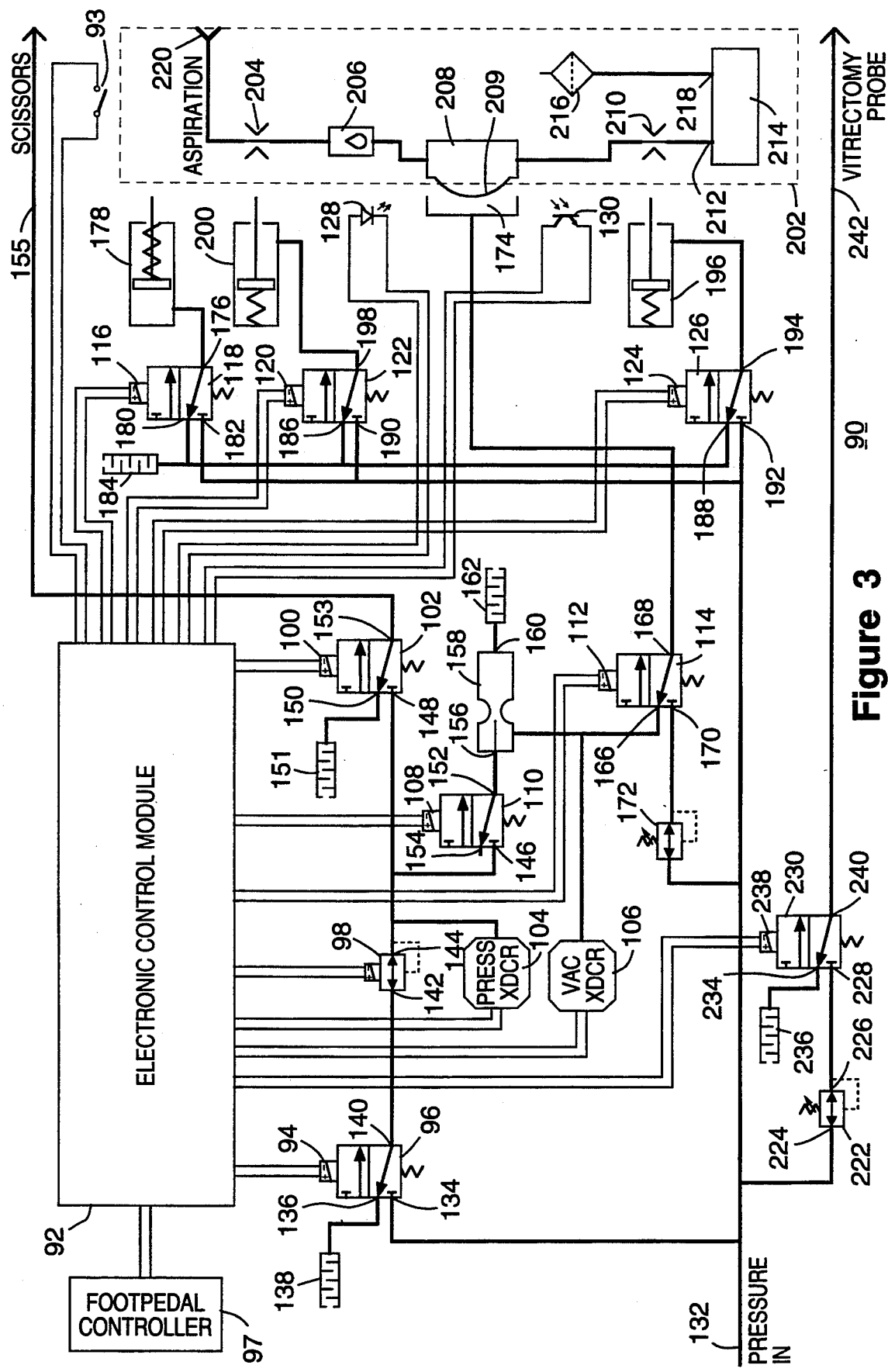
FIG. 3 is a schematic diagram of a suction and pressure control system of the present invention.

Referring now to FIG. 3 there is shown a suction and pressure control system 90. The suction pressure control system 90 consists of an electronic control module 92 which is connected to an aspiration cassette sensing switch 93, to a solenoid 94 of a first three-way valve 96. The electronic control module 92 is also connected to a footpedal controller 97, an electrical input of an electric/pressure transducer 98 and to a solenoid 100 of a second three-way valve 102. The electronic control module 92 is further connected to a pressure transducer 104 and a vacuum transducer 106. The electronic control module 92 is also connected to a solenoid 108 of a third three-way valve 110, to a solenoid 112 of a fourth three-way valve 114, to a solenoid 116 of a fifth three-way valve 118 and to a solenoid 120 of a sixth three-way valve 122. The electronic control module 92 is further connected to a solenoid 124 of a seventh three-way valve 126, to a light emitting diode 128 and to an NPN phototransistor 130. An input pressure line 132 is connected to an external air pump or other source of pressurized gas (not shown) and to a selectible input port 134 of the first three-way valve 96. Another selectible input port 136 of the first three-way valve 96 is connected to a muffler 138.

A port 140 of the first three-way valve 96 is alternately connected to either of the ports 134 or 136 through the action of the solenoid 94. The port 140 is also connected to a port 142 of the electric/pressure transducer 98. A port 144 of the electric/pressure transducer 98 is connected to the pressure transducer 104 and to an input port 146 of the third three-way valve 110 and to a selectible input port 148 of the second three-way valve 102. A port 150 of the second three-way valve 102 is connected to a muffler 151. A port 152 of the third three-way valve 110 is alternately connected to the port 146 and a port 154 through the action of the solenoid 108. A port 153 of the second three-way valve 102 is connected to an output pressure line 155.

The port 152 is also connected to a pressure port 156 of a venturi vacuum converter 158. An exhaust port 160 of the venturi 158 is connected to a muffler 162, while a vacuum port 164 of the venturi vacuum converter 158 is connected to both the vacuum transducer 106 and an input port 166 of the fourth three-way valve 114. A port 168 of the fourth three-way valve 114 alternately selects between the port 166 and a port 170 through the action of the solenoid 112. A mechanically set pressure regulator 172 is connected between the pressure input line 132 and the port 170 of the fourth three-way valve 114. The port 168 is connected to a pressure/vacuum chamber 174.

A port 176 of the fifth three-way valve 118 is connected to a pneumatic cylinder 178 and alternately to either a port 180 or a port 182 of the fifth three-way valve 116. The port 180 is connected to both a muffler 184 a port 186 of the sixth three-way valve 122 and to a port 188 of the seventh three-way valve 126. The port 182 is connected to a port 190 of the sixth three-way valve 122, the pressure input line 132 and to an input port 192 of the seventh three-way valve 126. A port 194 of the seventh three-way valve 126 is alternately connected between the ports 188 and 192 through the actuation of the solenoid 124. The port 194 is further connected to a pressure actuated cylinder 196. A port 198 of the sixth three-way valve 122 is alternately connected to either the port 186 or the port 190. The port 198 is also connected to a pressure actuated cylinder 200.

An aspiration cassette 202 includes a first pinch valve 204 which is connected to an inlet of a transparent drip chamber 206. An outlet of transparent drip chamber is connected to a fluid collection chamber 208. The fluid collection chamber 208 includes a flexible diaphragm 209 which is mounted across a rigid cylindrical opening. In the preferred embodiment of the invention, the diaphragm is constructed of rubber. The fluid collection chamber 208 is connected to a second pinch valve 212 which operates to open and close a fluid flow path between the fluid collection chamber 208 and an input port 212 of a fluid storage chamber 214. A hydrophobic filter 216 is connected to a vent 218 of the fluid storage chamber 214. An aspiration port 220 is connected to the inlet of the drip chamber 206 through the pinch valve 204.

While the suction and pressure system 90 is in a standby state, that is neither aspirating nor providing a modulated pressure to microscissors, the first three-way valve 96 is unenergized in order to prevent consumption of gas by the electric/pressure transducer 98, which transducer normally has a bleed flow even when its output pressure is zero. The third three-way valve 110 is utilized only for a suction control mode of operation, and is always unenergized while in a pressure control mode.

When the suction and pressure system 90 is in an active state, the first three-way valve 96 is energized. The pressure transducer 104 provides an electrical feedback signal which is utilized by the electronic control module 92 to drive the electric/pressure transducer 98 to thereby maintain the pressure sensed by the pressure transducer 104 at a desired level.

There are two different modes of control for pressure output. The first mode is a proportional mode wherein the third three-way valve 110 is always energized and the pressure delivered by the electric/pressure regulator 98 varies in response to control input from the footpedal controller 97. In a pulsed pressure mode, the electric/pressure regulator 98 delivers a constant pressure and the second three-way valve 102 is cycled through the solenoid 100 so as to alternately pressurize and vent to atmospheric pressure the output pressure line 155 which is connected to a surgical instrument such as microscissors. Typically such microscissors are driven by an air cylinder with a spring in opposition to the cylinder such that air pressure forces the scissors to close and the lack of air pressure allows the spring forces to reopen the blades of the scissors. It is generally considered that the safe mode for such microscissors is with the blades open.

In further detail, the electronic control module 92 alternately energizes the solenoid 100 to thereby toggle the port 153 between the output of the electric/pressure regulator 98 and atmosphere through the port 150 and the muffler 151.

In the proportional mode of operation, a surgeon will adjust the footpedal controller 97 to thereby provide a desired pressure level at the output pressure line 153 which is connected to a surgical instrument such as microscissors. The footpedal controller 97 is used to adjust the pressure to thereby control the opening and closing of the blades of the microscissors.

In the pulsed pressure mode of operation, the pressure level provided by electric/pressure regulator 98, and thereby the peak pressure at the output pressure line 153, is set by the surgeon through the electronic control module 92. The surgeon will adjust the footpedal controller 97 to either enable or disable the operation of the solenoid 100 so as to enable or disable the operation of a surgical instrument, such as microscissors, which is connected to output pressure line 153. In a first preferred embodiment, the surgeon will also adjust the footpedal controller 97 to control the frequency of the actuation of the solenoid 100 and thereby the frequency of opening and closing of the blades of the microscissors. In a second preferred embodiment, the frequency of operation of the solenoid 100 is set by the surgeon through the electronic control module 92.

Referring again to FIG. 3, a mechanically controlled pressure regulator 222 has an input port 224 connected to the input pressure line 132. The output port 226 of the regulator 222 is connected to a port 228 of an eighth three-way valve 230. The eighth three-way valve 230 has a port 234 which is connected to a muffler 236. The eighth three-way valve 230 also includes a solenoid 238 which is connected to the electronic control module 92. An output port 240 of the eighth three-way valve 230 selects from one of the ports 234 land 228. The port 240 is connected to an output line 242, which in the preferred embodiment of the invention is connected an opthalmics surgical instruments such as a vitrectomy probe.

In normal operation, a pulsed pneumatic pressure is provided on the output line 242 to drive a vitrectomy probe or other surgical instrument. The pressure regulator 222 delivers a constant pressure at an appropriate level for the instrument to be driven. The eighth three-way valve 230 is alternately energized, to thereby pressurize the output port 240, and unenergized, to vent the output port 240 to atmospheric pressure through the muffler 236.

This is essentially the same function as has been previously described for the pulsed pressure mode of operation for driving a pair of microscissors through the pressure output line 155. The pressure output line 155 could, in fact, be used to drive a vitrectomy probe. It is convenient, however, to have a dedicated pressure source for a vitrectomy probe, so that both microscissors and the vitrectomy probe are immediately available to the surgeon.

With reference now to the aspiration cassette 202, concurrent with the use of the vitrectomy probe, or any of several other surgical instruments, it is generally necessary to aspirate fluid and the excised tissue from within the eye. Such aspiration is accomplished by connecting a suitable aspiration probe to the aspiration port 220, and switching the mode of the electronic control module 92 to an aspiration mode, thereby venting to atmospheric pressure the pressure output line 153 through the port 150 and through the muffler 151.

In its suction mode, the suction and pressure control system 90 for a cassette 202 must first be inserted into the system 90. The fifth three-way valve 118 is unenergized and the sixth and seventh three-way valves 122 and 126 are energized such that the cylinders 178, 200 and 196 are each retracted. Once the aspiration cassette 202 is inserted the switch 93 signals the electronic control module 92 to go to a standby state. The fifth and seventh three-way valves 118 and 126 are energized and the sixth three-way valve 122 is unenergized so that the cylinder 178 is extended to thereby hold the aspiration cassette 202 in place and the cylinder 200 is extended to thereby close the pinch valve 204.

While in the standby state, a transfer cycle may be initiated. This consist of energizing the fourth three-way valve 114 for a period of time. This allows gas to flow from the pressure regulator 172 through the ports 170 and 168 of the fourth three-way valve 114 and into the chamber 174 thereby increasing the pressure in the chamber 174. This increased pressure is communicated through the diaphragm 209 to fluid within the chamber 208. This increased pressure causes fluid to flow from a chamber 208 through the pinch valve 210 and into chamber 214. As fluid flows out of the chamber 208, the diaphragm 209 is gradually displaced into the chamber 208. In the preferred embodiment of the invention, the diaphragm 209 fills the chamber 208, leaving air within the drip chamber 206. Air displaced by the fluid flowing into the chamber 214 is allowed to escape through the vent 218 through the hydrophobic filter 216 to atmosphere, thereby maintaining the chamber 214 at approximately atmospheric pressure. The purpose of this transfer cycle is to remove fluid from the chamber 208, enabling the chamber 208 to receive additional fluid during a succeeding aspiration phase. If desired, the hydrophobic filter 216 may be removed and instead the chamber 214 may be connected to a larger auxiliary chamber through a silicone tubing.

In the preferred embodiment of the invention volume of the chamber 208 is approximately 50 cubic centimeters to allow the rapid change one vacuum level to a desired vacuum level at the aspiration port 220. In the preferred embodiment of the invention the volume of the chamber 214 is approximately 250 cubic centimeters, which is significantly larger than the volume of the chamber 208.

While in the standby state, whether transferring fluid from the chamber 208 to the chamber 214 or simply waiting, the first three-way valve 96 is unenergized in order to prevent consumption of gas by the electric/pressure regulator 98, which regulator normally has a bleed flow even with its output pressure at zero. The second three-way valve 98 is used only for the pressure control mode of operation and is always unenergized while in the system 90 is in the suction control mode. The third three-way valve 110 is unenergized in the standby state, since this helps to vent the chamber 174 to atmospheric pressure more quickly when the standby state is entered.

When in the active state, the first three-way valve 96 and the third three-way valve 110 are energized, allowing flow through the venturi vacuum converter 158 under the control of the electric/pressure regulator 98. The fourth three-way valve 126 is unenergized thereby connecting the vacuum port 164 of the venturi vacuum converter 158 to the chamber 174. The vacuum port 164 is also connected to the vacuum transducer 106 to thereby provide an electrical feedback signal which is used by the electronic control module 92 to drive the electric/pressure regulator 98 so as to maintain the vacuum sensed by the vacuum transducer 106 at a desired level.

In the active state the sixth three-way valve 122 is energized to retract the cylinder 200 to thereby open the pinch valve 204. The seventh three-way valve 126 is unenergized to extend the cylinder 196 to thereby the pinch valve 210. Vacuum in the chamber 174 is communicated through the diaphragm 209. In the active state the sixth three-way valve 122 is energized to retract the cylinder 200 to thereby open the pinch valve 204. The vacuum in the chamber 174 is communicated through the diaphragm 209 to the fluid in the chamber 208. This decreased pressure causes fluid to flow from a surgical instrument connected to the aspiration port 220 of the aspiration cassette 202, through the pinch valve 204 through the drip chamber 206 and into the chamber 208. In the preferred embodiment of the invention the drip chamber 206 is transparent to thereby provide the surgeon with a visual confirmation of fluid flow.

As fluid flows into the chamber 208, the diaphragm 209 is gradually displaced into the chamber 174. The diaphragm 209 is of a bellows configuration which allows an insignificantly small pressure difference between the chambers 208 and 174 to move the diaphragm 209. Thus, the pressure in the chamber 208 is approximately the same as the pressure in the chamber 174 as long as the diaphragm 209 is free to move. Once the diaphragm 209 moves in contact with the wall of chamber 174, however, the vacuum level in the chamber 208 would begin to fall below that in the chamber 174. To prevent this, the light emitting diode 128 and the NPN phototransistor 130 are arranged such that the diaphragm 209 interrupts the optical path between the LED 128 and the NPN photo transistor 130 shortly before the diaphragm 209 contacts the wall of the chamber 174. This forces the system 90 to enter the standby state and initiate a transfer cycle. Upon such initiation the surgeon is immediately provided warning that the transfer cycle has commenced. In the normal course of most ophthalmic surgery, a surgeon will not aspirate a volume greater than 25 cubic centimeters without first lifting his or her foot from the footpedal.

Figure 4:
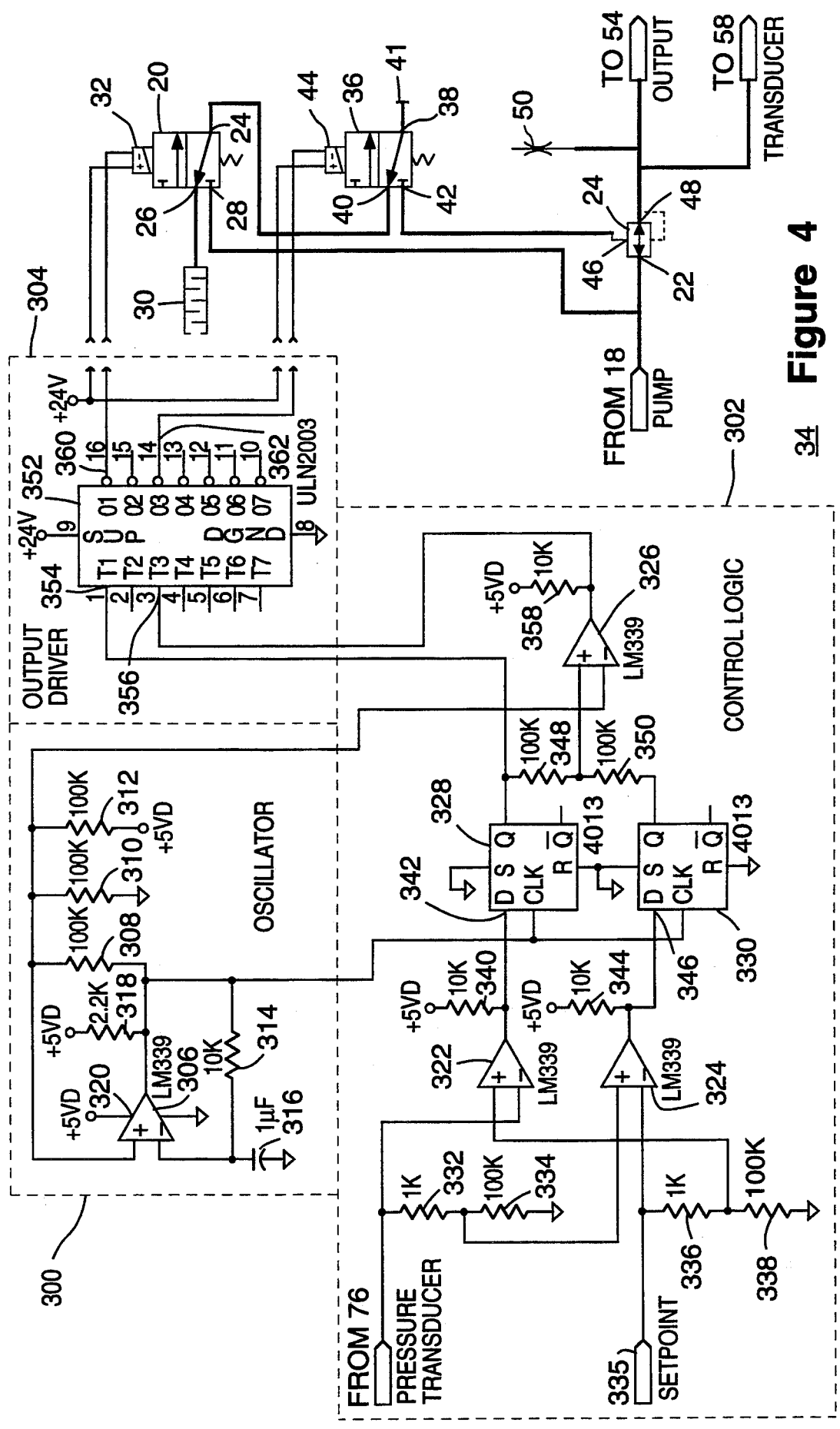
FIG. 4 is a schematic diagram of the electronic control module of FIGS. 1 and 2.

Referring now to FIG. 4 there is shown the electronic control module 92 of the gas delivery system 10 of the present invention. The module consists of three sub-modules, an oscillator sub-module 300, a control logic sub-module 302 and an output driver sub-module 304. The oscillator module 300 includes a op-amp 306 having its non-inverting input connected to the junction of a resistor 308, a resistor 310 and a resistor 312. The inverting input of the op-amp 306 is connected to the junction of a resistor 314 and a capacitor 316. The output of the op-amp 306 is connected to the junction of a resistor 318 and the resistor 314. A 5-volt potential is applied to a power input port 320 of the op-amp 306 and also to one end of the resistor 318. The control logic sub-module 302 consists of a first comparator 322, a second comparator 324, a third comparator 326, a first latch 328 and a second latch 330. The pressure transducer 76 of FIG. 1 is connected to the junction of a resistor 332 and the inverting input of the comparator 322. The resistor 332 together with a resistor 334 form a resistive voltage divider having its output connected to the non-inverting input of the comparator 324. A setpoint input 335, is connected to the junction of a resistor 336 and the inverting input of the comparator 324. The resistor 336 together with a resistor 338 for a resistive voltage divider having its output connected to the non-inverting input of the comparator 322. The output of the comparator 322 is connected to the junction of a resistor 340 and a delay input 342 of the latch 328. The output of the comparator 324 is connected to the junction of a resistor 344 and a delay input 346 of the latch 330. The non-inverting output of the latch 328 is connected to a resistor 348. The non-inverting output of the latch 330 is connected to a resistor 350. The junction of the resistors 348 and 350 is connected to the non-inverting input of the comparator 326. The output driver 304 consists of a multiple driver 352 having a first input 354 connected to the junction of the non-inverting output of the latch 328 and the resistor 348. A second driver input 356 is connected to the junction of a resistor 358 and the output of the comparator 326. A first inverted output 360 of the driver 352 is connected to the solenoid 32. A second inverted output 362 of the driver 352 is connected to the solenoid 44.

Referring again to the oscillator sub-module 300, the output of the comparator 306 is connected to the clock input of both the latch 328 and the latch 330. The non-inverting input of the op-amp 306 is connected to the inverting input of the op-amp 326.

The oscillator sub-module 300 generates two signals which are utilized by the control logic sub-module. The first signal which is present at the output of the op-amp 306 switches between 0 and 5 volts and is fed to the clock input of both the latch 328 and the latch 330. A second signal which is present at the junction of the non-inverting input of the op-amp 306 and the resistors 308, 310 and 312, switches between 1.7 volts and 3.3 volts. Both signals are square waves of approximately 50% duty cycle at a frequency of approximately 100 hertz.

In the control logic sub-module 302 an analog signal representing the actual pressure measured by the pressure transducer 76 is compared against the analog signal representing the setpoint. If the actual pressure is <99% of the setpoint, the output of the op-amp (comparator) 322 is set high. If 99% of the actual pressure is greater than the setpoint (i.e., the actual pressure is >101% of the setpoint), the output of the op-amp 324, which also acts as a comparator, is set high. Otherwise, if the actual pressure is between 99% and 101% of the setpoint, the outputs of both the op-amp 322 and the op-amp 324 remain low.

The outputs of the comparator 322 and the comparator 324 are periodically sampled and latched by the latches 328 and 330 respectively. The sampling occurs on the rising edge of the square wave signal present at the output of the op-amp 306. The resistors 348 and 350 produce a signal at the non-inverting input of the comparator 326 which is approximately 2.5 volts, if the output of either the latch 328 or the latch 330 is high, and is 0 volts when both such outputs are low. In the latter case (which corresponds to the actual pressure being between 99% and 101% of the setpoint), the output of the comparator 326 is continuously low, since the signal at the inverting input of the comparator 326 is always >0. If the actual pressure is not between 99% and 101% of the setpoint, then the output of either the latch 328 or the latch 330 will go high at the rising edge of the square wave signal from the output of the op-amp 306, causing a level of 2.5 volts at the non-inverting input of the comparator 326. At this time, the signal at the inverting input of the comparator 326 is also at its high level of 3.3 volts, causing the output of the comparator 326 to remain low. When the square wave signal at the inverting input of the comparator 326 switches to its low level of 1.7 volts, the output of the comparator 326 goes high.

Thus, the output of the comparator 326 remains low while the actual pressure is between 99% and 100% of the setpoint, it otherwise cycles between low and high at a rate established by the frequency of the square wave signal which is provided to the latches 328 and 330 and at a slightly reduced potential to the inverting input of the comparator 326.

The output of the latch 328 is high when the actual pressure is less than 99% of the setpoint. The output driver 352 energizes the first three-way valve 20 when the output of the latch 328 is high and energizes the second three-way value 36 when the output of the comparator 326 is high. When the actual pressure is between 99% and 101% of the setpoint the second three-way valve 336 is unenergized, so that the pressure at the pilot chamber port 46, and thus the pressure within the pilot chamber of the piloted pressure regulator 24, cannot change. When the actual pressure is <99% of the setpoint, the second three-way valve 36 cycles and the first three-way valve 20 is energized to connect the second three-way valve 36 to the pump output 18 (of FIG. 1). Each cycle of the second three-way valve 36 will slightly increase the pressure at the pilot chamber port 46 and thus increase the pressure within the pilot chamber of the piloted pressure regulator 24, thereby increasing the pressure at the output port 48 of the piloted pressure regulator 24. When the actual pressure >101% of the setpoint, the second three-way valve 36 cycles and the first three-way valve 20 is unenergized to thereby connect the second three-way valve 36 to atmospheric pressure through the muffler 30. Each cycle of the second three-way valve 36 will slightly decrease the pressure within the pilot chamber of the piloted pressure regulator 24 and hence decrease the pressure at the output port 48 of the piloted pressure regulator 24.

Figure 5:
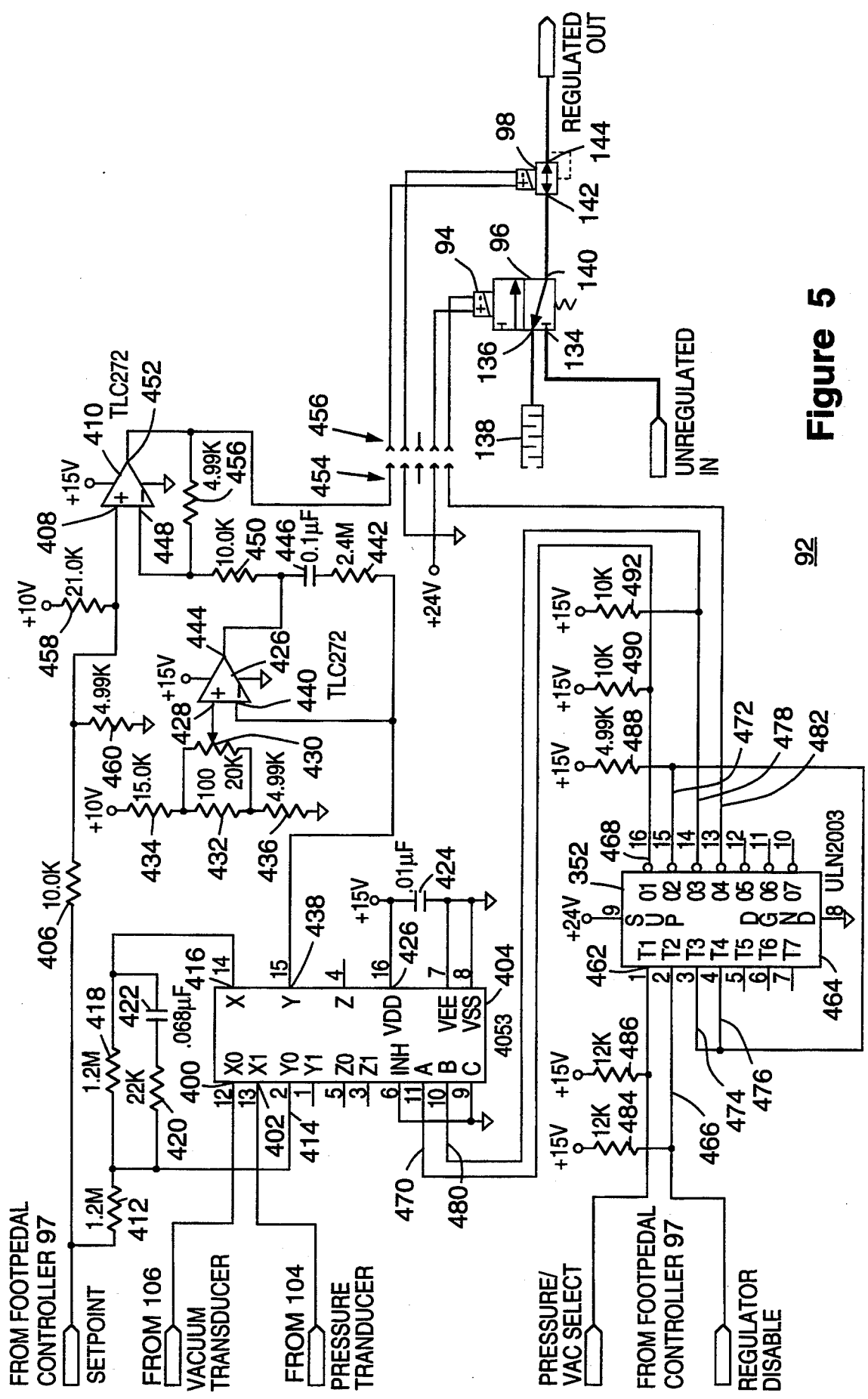
FIG. 5 is a schematic diagram of the electronic control module of FIG. 3.

Referring now to FIG. 5, there is shown a detailed schematic diagram of the electronic control module 92 of FIG. 3. The vacuum transducer 106 of FIG. 3 and the pressure transducer 104 of FIG. 3 are connected to an input 400 and input 402, respectively, of an analog switch 404. A setpoint signal is provided from the footpedal controller 97 through a resistor 406 to the non-inverting input 408 of an integrator (operational amplifier) 410. The setpoint signal is also provided through a resistor 412 to an input 414 of the analog switch 404. An output 416 of the analog switch 404 is coupled to a resistive capacitive network consisting of a resistor 418, a resistor 420 and capacitor 422. A capacitor 424 provides filtering at a power input port 426 of the analog switch 404. An integrator (operational amplifier) 426 has a non-inverting input 428 connected to center arm of a rheostat 430. The ends of the rheostat 430 are connected across a resistor 432 which together with resistors 434 and 436 form a voltage divider network. An output 438 of the analog switch 404 is connected to junction of an inverting input 440 of the integrator 426 and a resistor 442. The other end of the resistor 442 is coupled to an output 444 of the integrator 426 through a capacitor 446. The output 444 is further connected to an inverting input 448 of the integrator 410 through a resistor 450. An output 452 of the integrator 410 is coupled to the electric pressure transducer 98 through a five-wire plug 454 and a five-wire socket 456. A resistor 458 and a resistor 460 together form a voltage divider network which operates to provide a bias at the non-inverting input 408.

A pressure/vacuum select signal is provided to an input 462 of a driver 464. A regulator disable signal is provided to an input 466 of the driver 464. The pressure/vacuum select signal and the regulator disable signal are digital logic signals which are derived from human operator input. The setpoint signal is an analog signal which is derived from human operator input. An inverting output 468 of the driver 464 provides an inverted signal to an input 470 of the analog switch 404. An inverted output 472 of the driver 464 is coupled to the junction of an input 474 and 476 of the driver 464. An output 478 of the driver 464 is connected to an input 480 of the analog switch 404. An inverted output 482 of the driver 464 is connected to the solenoid 94 of the first three-way valve 96. A set of resistors 484, 486, 488, 490 and 492 each have one end connected to a +15 volts DC power supply to thereby bias either inputs or outputs of the driver 464. In particular, the resistor 484 operates to bias the input 466. The resistor 486 operates to bias the input 462. The resistor 488 operates to bias the inverting output 472 and the inputs 474 and 476. The resistor 490 operates to bias the inverting output 468. And, the resistor 492 operates the bias the output port 478. In operation, signals from the vacuum transducer 106 and the pressure transducer 104 are offset and inverted, so that when the actual vacuum or pressure is equal to the setpoint, the corresponding transducer signal is equal to five volts minus the setpoint signal.

The driver 464 operates to convert digital input signals from five volt logic levels to the fifteen volt logic levels necessary to drive the analog switch 404. The driver 464 is also used to invert logic signals and to drive the solenoid 94 of the first three-way valve 96. The regulator disable signal, when high, turns off the first three-valve 96 in order to prevent consumption of gas when the system 10 is inactive, and also opens analog switch 404, in order to prevent the integrator 426 from changing its output while the system 10 is inoperative.

The pressure/vacuum select signal drives the analog switch 404 to select from either the vacuum transducer 106 (for pressure/vacuum select high) or the pressure transducer 104 (for pressure/vacuum select low) as the feed back signal.

Pressure versus voltage relationship of the electric/pressure transducer 98 is known approximately. The vacuum versus pressure relationship for the venturi vacuum convertor 158 is also known approximately. The signal levels of the vacuum transducer 106 and the pressure transducer 104 have been selected such that the level of these two signals are approximately equal. The amplifier formed by the integrator 410 and the resistors 456, 458, 460, 450 and 406 is arranged to provide the approximate gain and offset such that, with the output of the integrator 426 fixed, a change in the setpoint signal produces a change in the output of the integrator 410, which output is approximately the correct level to drive electric/pressure transducer 98 to thereby produce or pressure or vacuum corresponding to the setpoint signal. In other words, this part of the circuit acts as an open loop control system.

Closed loop compensation for residual errors in the open loop control system is provided by the integrator 426. The bias to the non-inverting input 428 is approximately 2.5 volts, and is adjustable in order to compensate for the input offset voltage of the integrator 426 and for any mismatch in the resistors 412 and 418. The potentiometer 430 adjusted such that the output 444 of the integrator 426 holds a constant level when the selected transducer feedback signal is exactly equal to five volts minus the setpoint signal. If the transducer feedback signal is higher than this, indicating that the actual pressure or vacuum is less than the setpoint, then the output 444 of the integrator 426 decreases over time at a rate proportional to the magnitude of the error. This decrease in the output of the integrator 426 causes an increase in the output 452 of the op-amp 410, which in turn drives the electric/pressure transducer 98 to increase the output pressure or vacuum at the output 144. Conversely, a transducer feedback signal corresponding to an actual pressure or vacuum greater than the setpoint will drive the electric pressure transducer 98 to decrease the output pressure or vacuum.

The basic integrator circuit for the integrator 426 consists an op-amp 426, the capacitor 446 and the resistors 412 and 418. The capacitor 422 and the resistors 420 and 442 do not affect the steady state response, but provide phase compensation to improve the transient response of the system 10.

Figure 6:
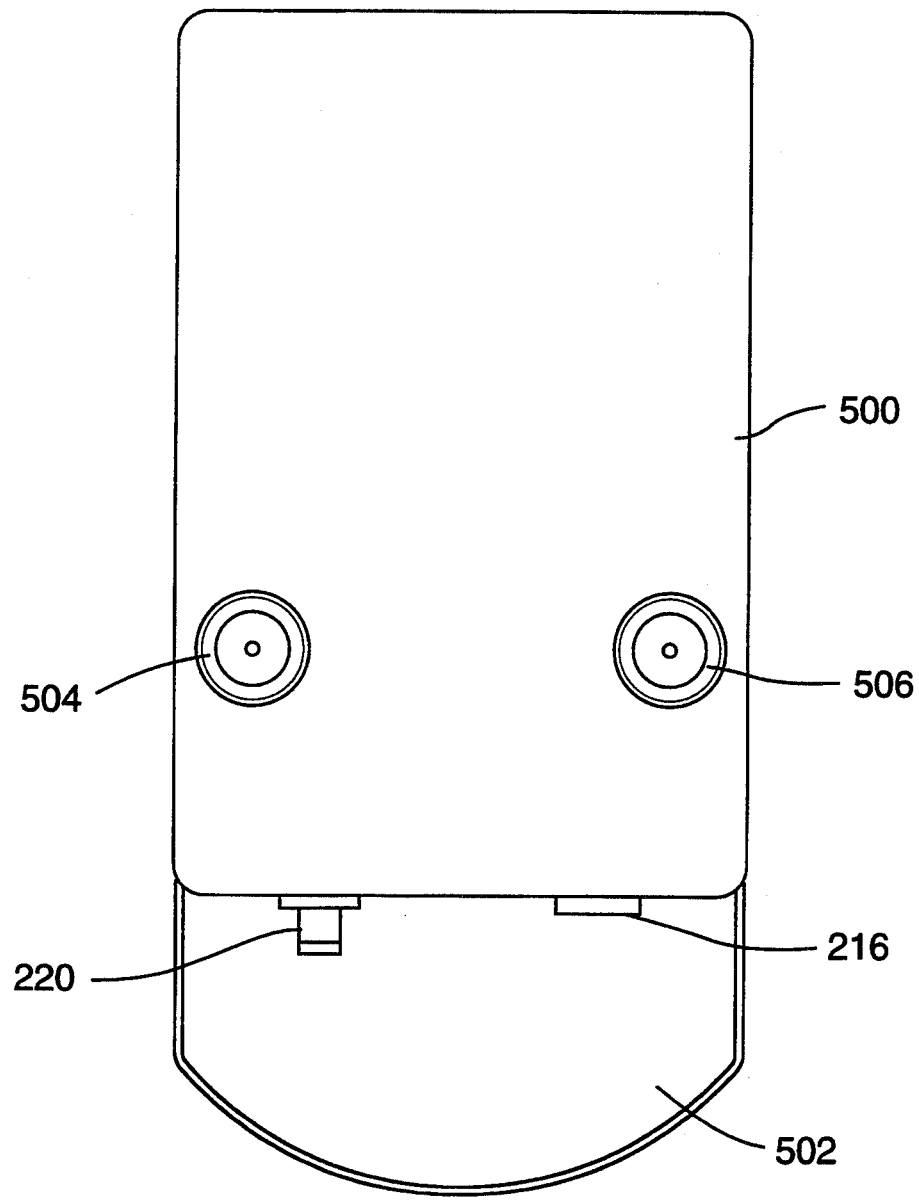
FIG. 6 is a top plan view of an aspiration cassette of the present invention.

FIG. 6 shows a top plan view of the aspiration cassette 202. The aspiration cassette 202 includes a top surface 500 and a molded handle 502. Mounted in the top surface 500 are a first soft rubber grommet 504 and a second soft rubber grommet 506. These flexible grommets 504 and 506 are designed to apply force from the cylinders 196 and 200 through the top surface 500, with little resistance while maintaining a spill proof seal for the chamber 214. The inlet 220 is mounted perpendicular to the top surface 500. Similarly the filter 216 is also mounted perpendicular to the top surface 500.

Figure 7:
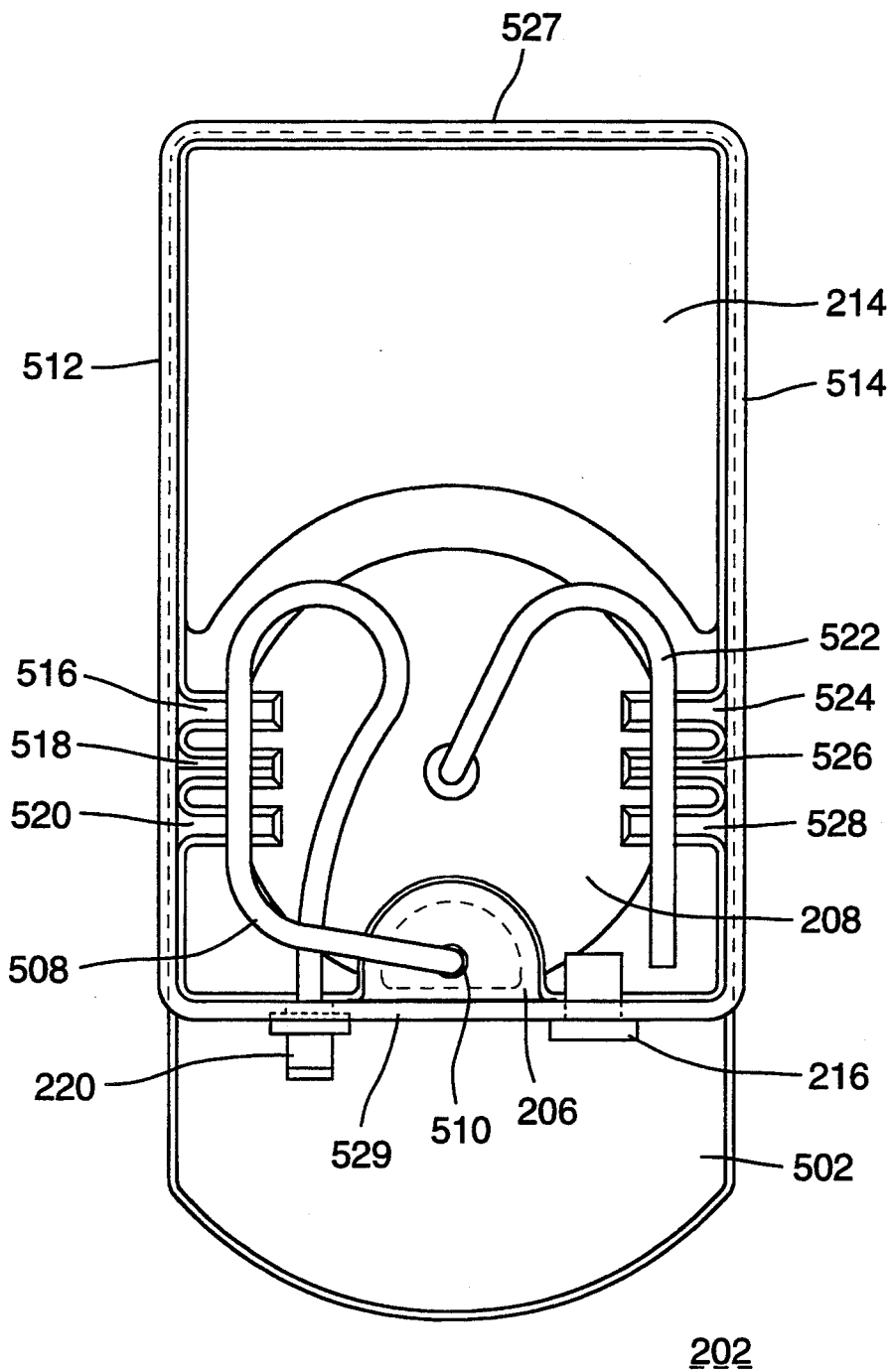
FIG. 7 is a top plan sectional view of the aspiration cassette of FIG. 6.

Referring now to FIG. 7, which shows a plan sectional top view of the aspiration cassette 202, and to FIG. 3, the aspiration port 220 is connected to one end of a silicone tubing 508. The other end of the silicone tubing 508 is connected to an inlet 510 of the drip chamber 206. A pair of longitudinal walls 512 and 514 of the aspiration cassette 202 each include a plurality of projections which function together with the grommets 504 and 506 to act as the pinch valves 204 and 210. In further detail the longitudinal side wall 512 includes a projection 516, a projection 518 and a projection 520 upon which is mounted a relatively linear section of the silicone tubing 508. A second silicone tubing 522 has a first end connected to the top and center of the chamber 208 and its other end terminating within a volume which defines the chamber 214. A relatively linear section of the silicone tubing 522 rests upon a projection 524, a projection 526 and a projection 528 which projections are attached to the longitudinal wall 414.

Referring now to FIGS. 3, 6 and 7 the pinch valve 204 consists of the flexible grommet 504, the projections 516, 518 and 520 and the section of the silicone tubing 508 which rests upon such projections. In operation when the cylinder 200 is extended, a cylindrical shaft from the cylinder 200 presses against the flexible grommet 506 such that the grommet 506 in conjunction with the projections 516, 518 and 520 compress the silicone tubing 422 thereby pinching or closing the path through the inner diameter of the silicone tubing 508.

In a similar manner the flexible grommet 506, the projections 524, 526 and 528 together with the linear section of the silicone tubing 522 which rests upon such projections together form the pinch valve 210. In this case the cylinder 196 includes a cylindrical shaft as shown in FIG. 3 which presses against the flexible grommet 506.

The cylinder 178 when extended pushes against a retaining plate which holds the aspiration cassette 202 in a fixed position and thereby aligning the shaft of each of the cylinders 196 and 200 with the flexible grommets 506 and 504 separately. A first transverse wall 527 connects to one end of each of the longitudinal walls 512 and 514 and a bottom surface 534. A second transverse wall 529 connects to the opposite end of each of the longitudinal walls 512 and 514 and to the bottom surface 534.

Referring now to FIGS. 3, 8, 9 and 10 the diaphragm 209 consists of a flexible elastomer which is positioned across the chamber 208 and secured to the bottom surface 534. Referring again to FIG. 8 the drip chamber 206 has its inside upper surfaces shaped in the form of an inverted notch. In further detail, at a junction 530 of the upper inside surface of the drip chamber 206 and a nipple 532, the junction 530 is positioned lower than the surrounding upper inside wall. This shape promotes the formation of single droplets which fall through the drip chamber to thereby provide a visual indication of the aspiration rate of fluids and excised tissue. If the upper inside surface of the drip chamber 206 were planar, fluids entering through the nipple 532 would cling to the upper surface of the drip chamber and then flow along the vertical walls of the drip chamber as they are pulled by gravity.

Figure 8:
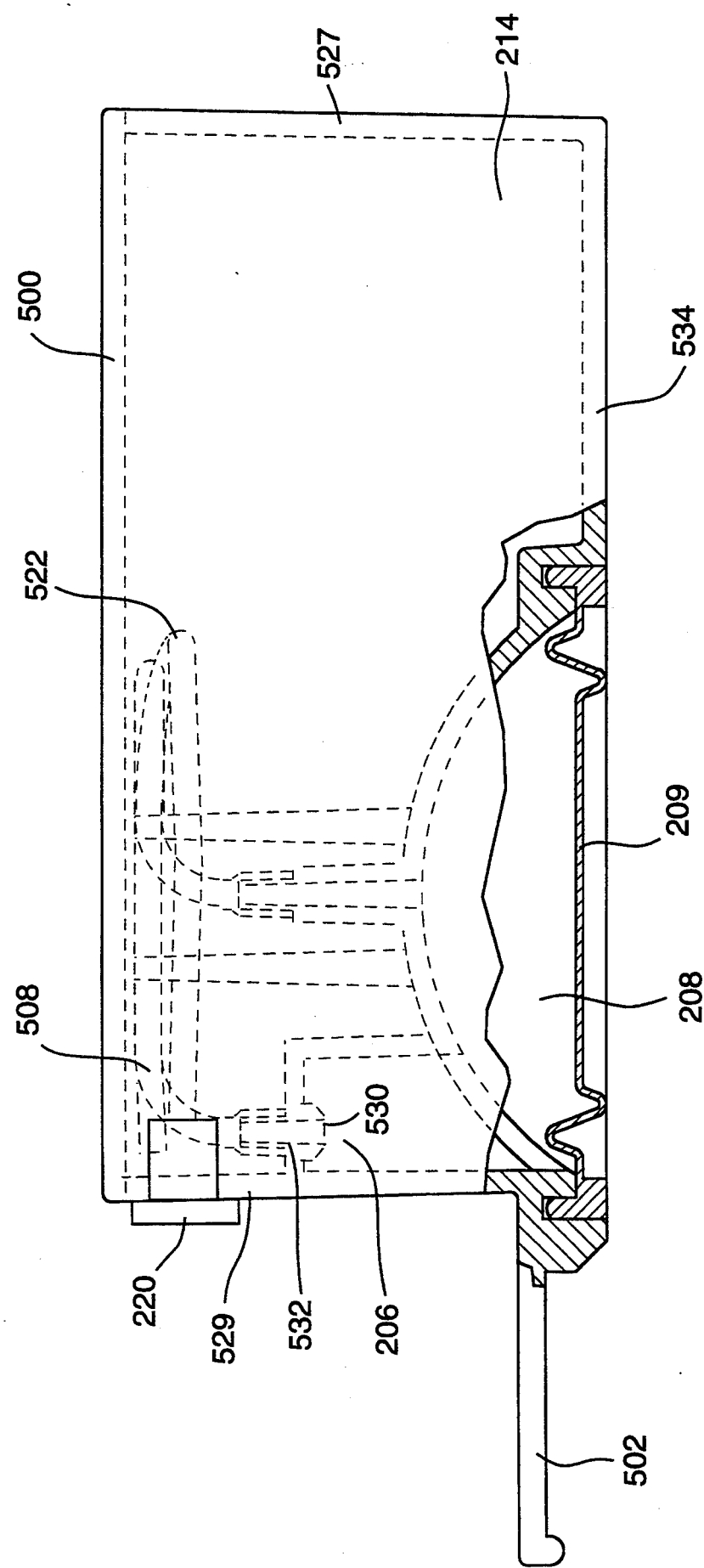
FIG. 8 is a fragmentary side elevational view of the aspiration cassette of FIG. 6.
Figure 9:
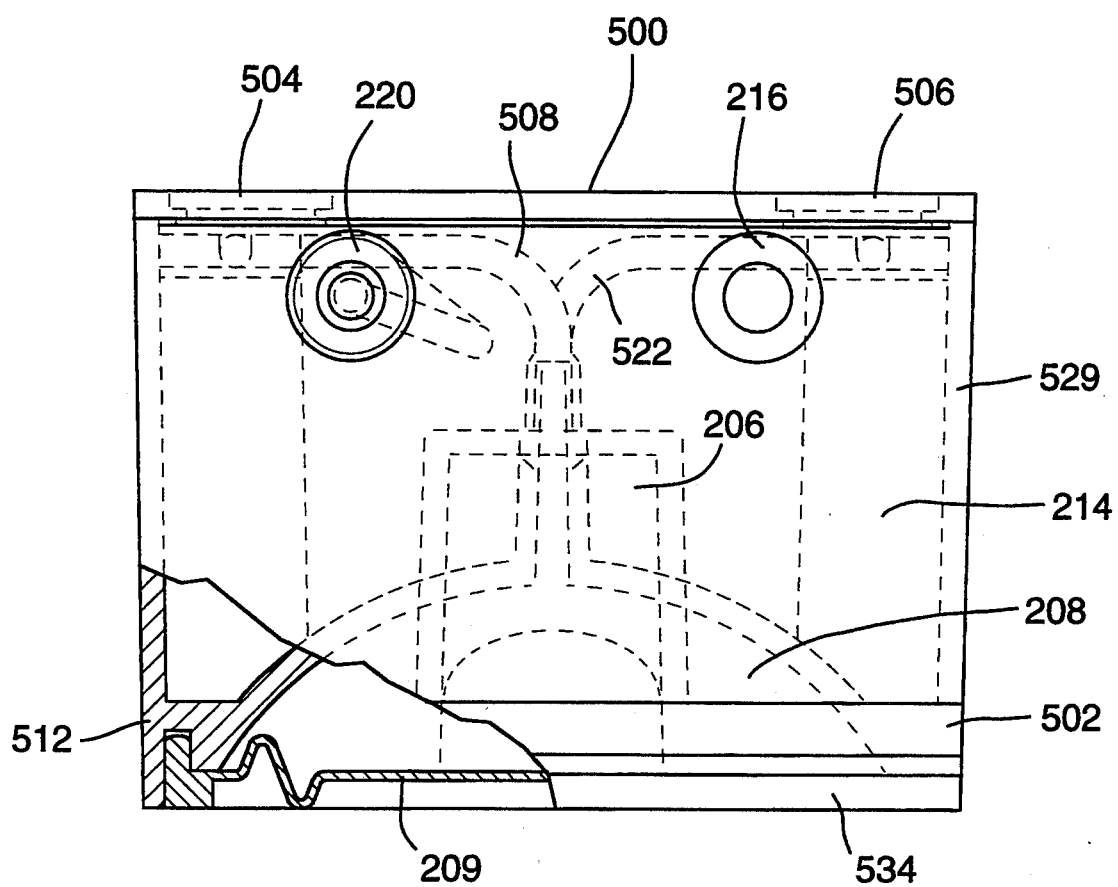
FIG. 9 is a fragmentary front elevational view of the aspiration cassette of FIG. 6.

As clearly shown in FIGS. 8 and 9 the volume of the chamber 208 is significantly smaller than the volume of the chamber 214. As previously described the use of a small volume for the chamber 208 provides for more rapid changes in the level of vacuum at the aspiration port 220 which response times can be critical during ophthalmic surgery.

Figure 10:
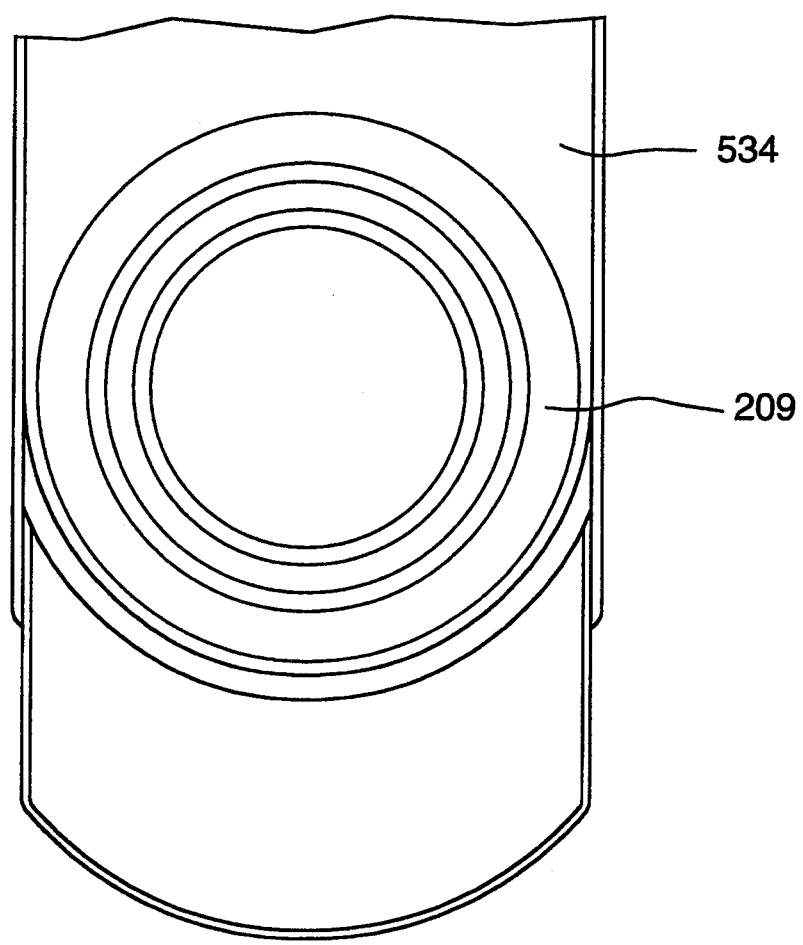
FIG. 10 is a partial bottom plan view of the aspiration cassette of FIG. 6.

Referring now to FIG. 10, the diaphragm 209 of the aspiration cassette 202 is substantially circular with concentric circular corrogations to allow for expansion of the diaphragm into the chamber 208 and into the chamber 174.

Figure 11:
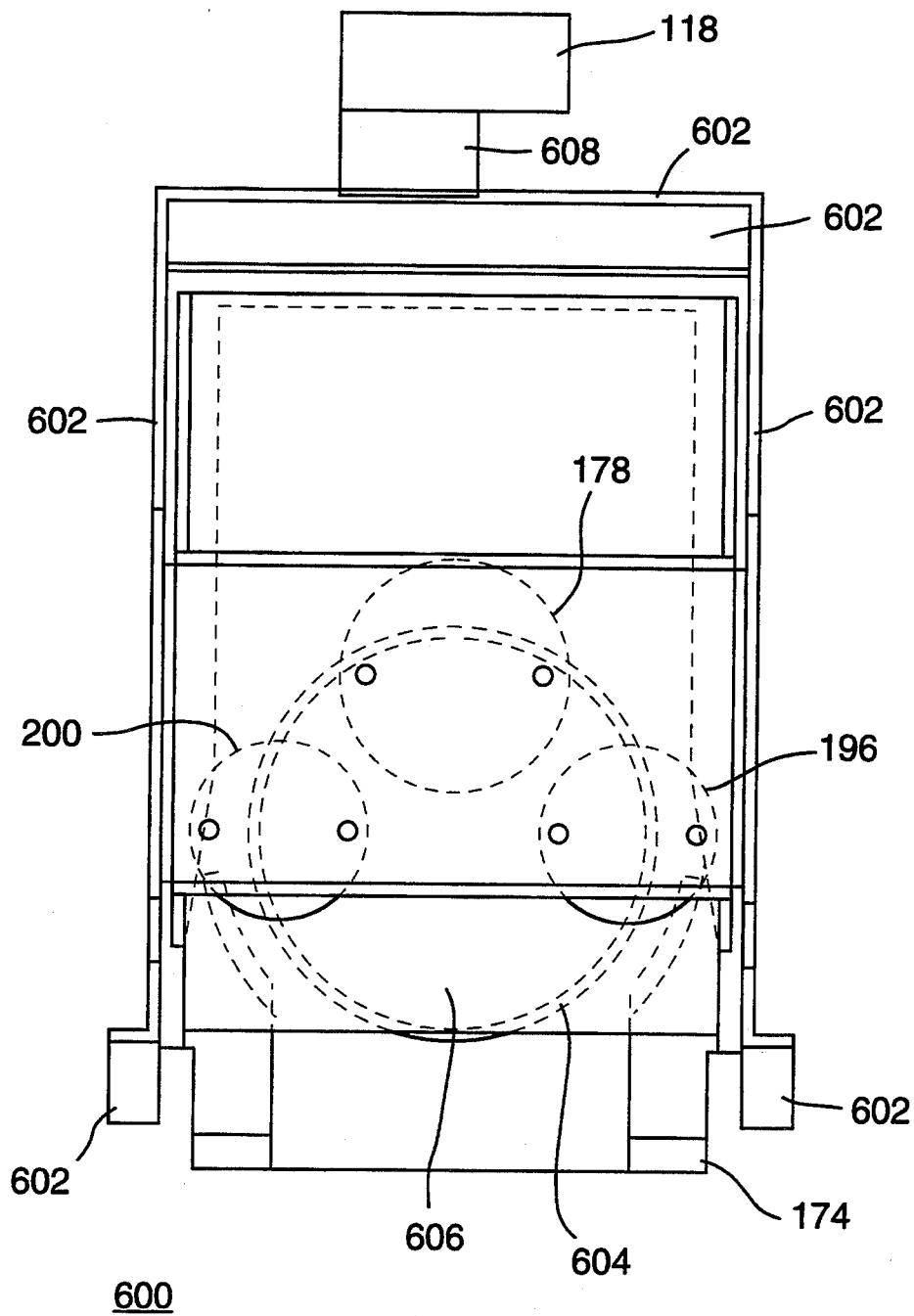
FIG. 11 is a top sectional plan view of an aspiration cassette retaining mechanism of the present invention.

Referring now to FIG. 11, there is shown a top plan view of a cassette retaining mechanism 600. The cassette retaining mechanism 600 includes an outer shell 602. The cassette retaining mechanism 600 also includes the chamber 174 of FIG. 3, a chamber lip 604 and a chamber opening 606. The cylinders 196 and 200 are disposed on opposite sides of the cassette retaining mechanism 600. The three-way valve 118 and a manifold 608 are located at the opposite end of the mechanism 600 from the chamber 174. As is apparent from FIG. 11, the shell 602 is shaped to approximate the shape of the aspiration cassette as shown in FIGS. 6 through 10.

Figure 12:
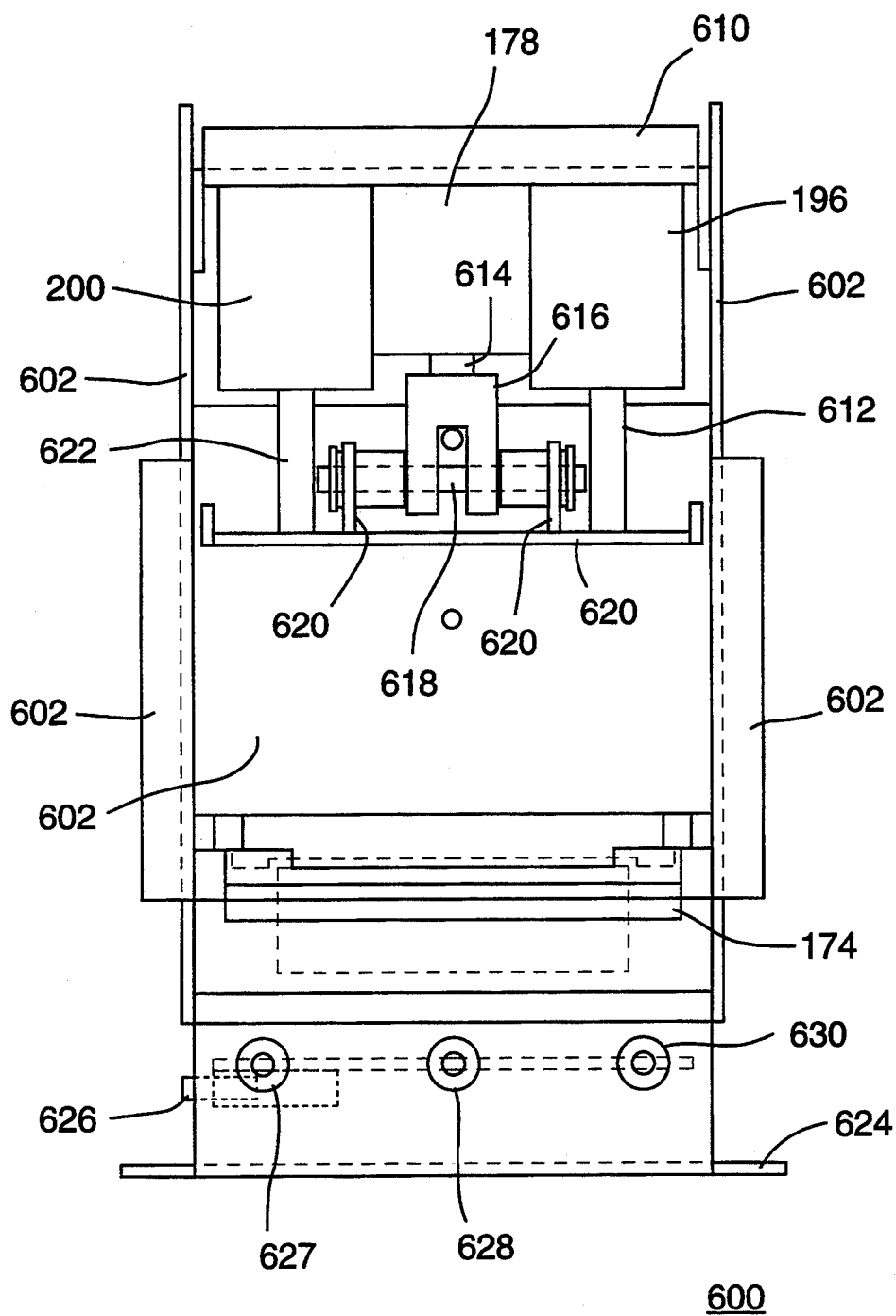
FIG. 12 is a front plan view of the aspiration cassette retaining mechanism of FIG. 11.

Referring now to FIG. 12, the cylinders 178, 196 and 200 are mounted to a cylinder bracket 610. The cylinder 196 is internally connected to a transfer pinch cylinder shaft 612. As previously described, this transfer pinch cylinder shaft 612 selectively closes the pinch valve 210. The cylinder 178 is internally connected to a clamp cylinder shaft 614. The clamp cylinder shaft 614 is connected to a clevis 616. A dowel pin 618 securely connects the clevis 616 to a clamp plate 620. The cylinder 200 is internally connected to an aspiration pinch cylinder shaft 622. The aspiration pinch cylinder shaft 622, as previously described with respect to FIG. 3, operates to selectively close the pinch valve 204. The cassette receiving mechanism 600 includes a base bracket 624 and a 10-pin interface connector 626. The cassette receiving mechanism 600 also includes a first luer connector 627 which in the preferred embodiment of the invention is utilized to connect a tubing to a vitrectomy probe. The cassette retaining mechanism 600 also includes a second luer connector 628 which in the preferred embodiment of the invention is connected to a pneumatic line which terminates at a set of micro-scissors. The cassette retaining mechanism 600 further includes a third luer connector 630 which in the preferred embodiment of the invention is utilized to provide pressurized gas for a fluid-gas exchange.

Figure 13:
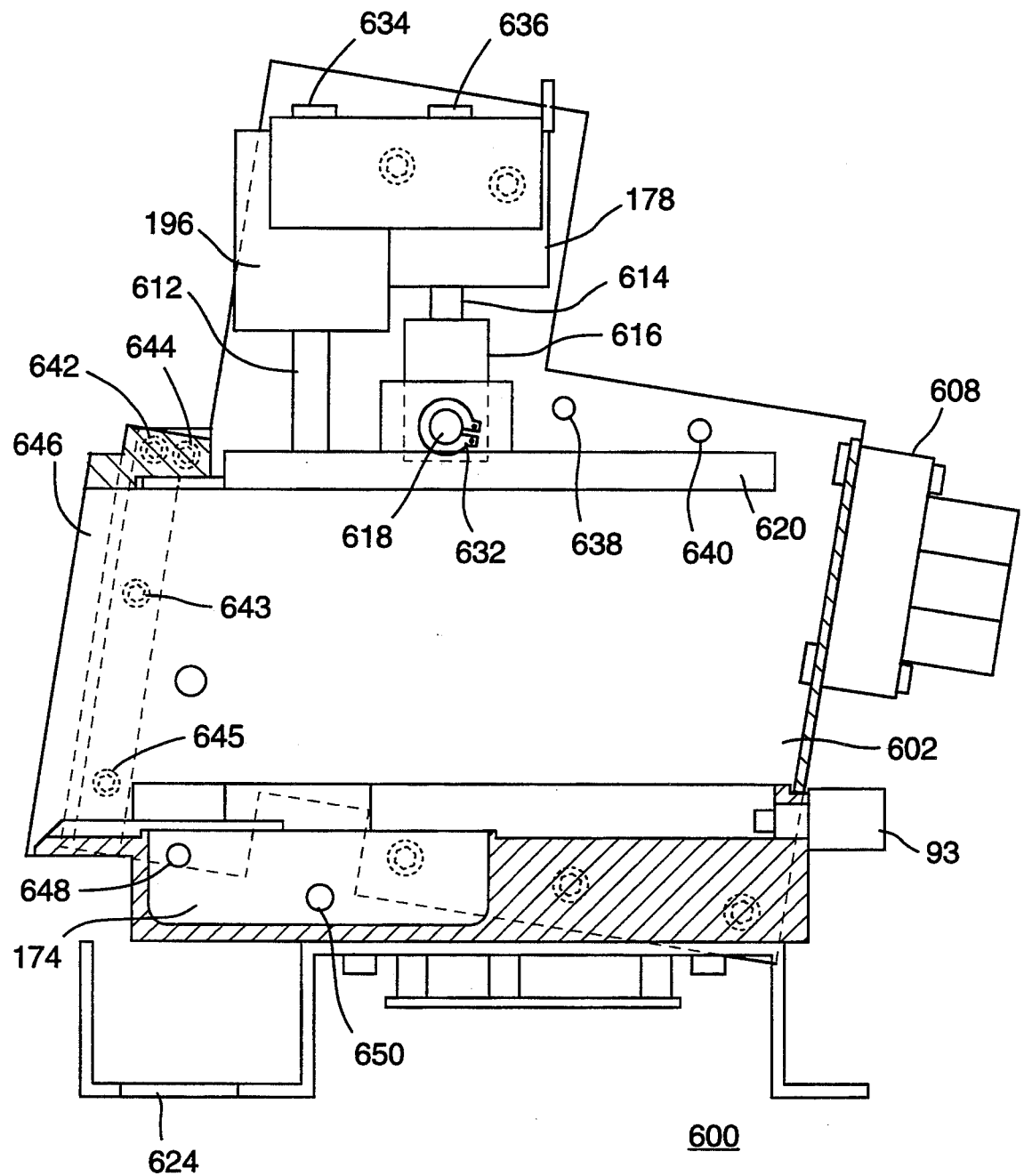
FIG. 13 is a partial side plan view of the aspiration cassette retaining mechanism of FIG. 11.

Referring now to FIG. 13, a side plan view of the cassette retaining mechanism 600 is shown. An E-clip fastener 632 retains the dowel pin 618 in position through the clevis 616. The cassette sensor switch 93 is mounted below the manifold 608. A pair of fasteners 634 and 636 secure the cylinders 200 and 196 to the cylinder bracket 610 of FIG. 12. A pair of bores 638 and 640 are utilized to mount a clamp plate guide (shown in FIG. 16). A pair of fasteners 642 and 644 and 643 and 645 fasten a bezel 646 to the shell 602. Three of the solenoid valves of FIG. 3 are mounted onto the manifold 608. A chamber port 648 provides passage to the chamber 174. The LED 128 and the photo transistor 130 are located within the bore 650.

Figure 14:
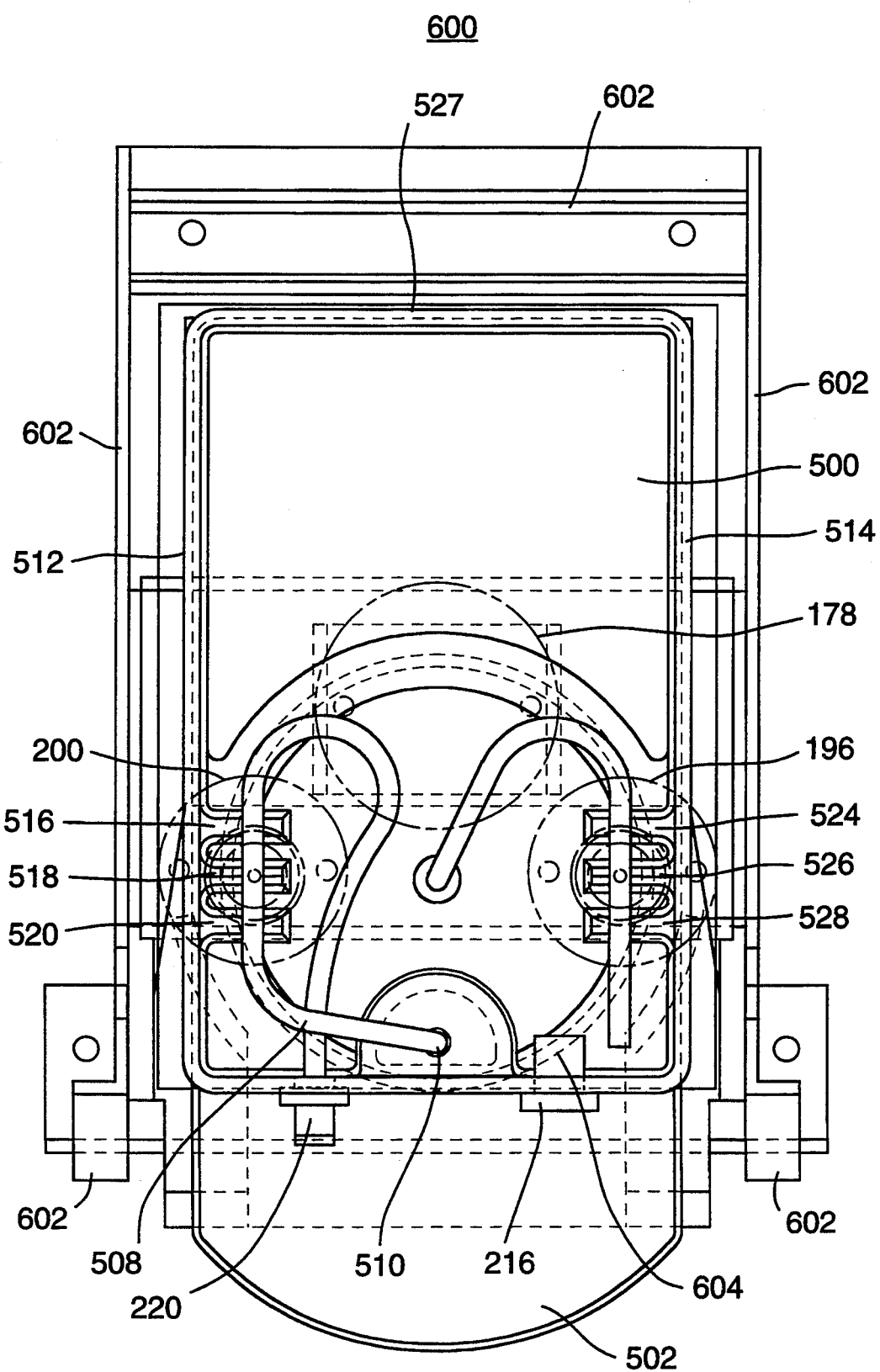
FIG. 14 is a top plan sectional view of the aspiration cassette of FIG. 6 as mounted in the aspiration cassette retaining mechanism of FIG. 11.
Figure 15:
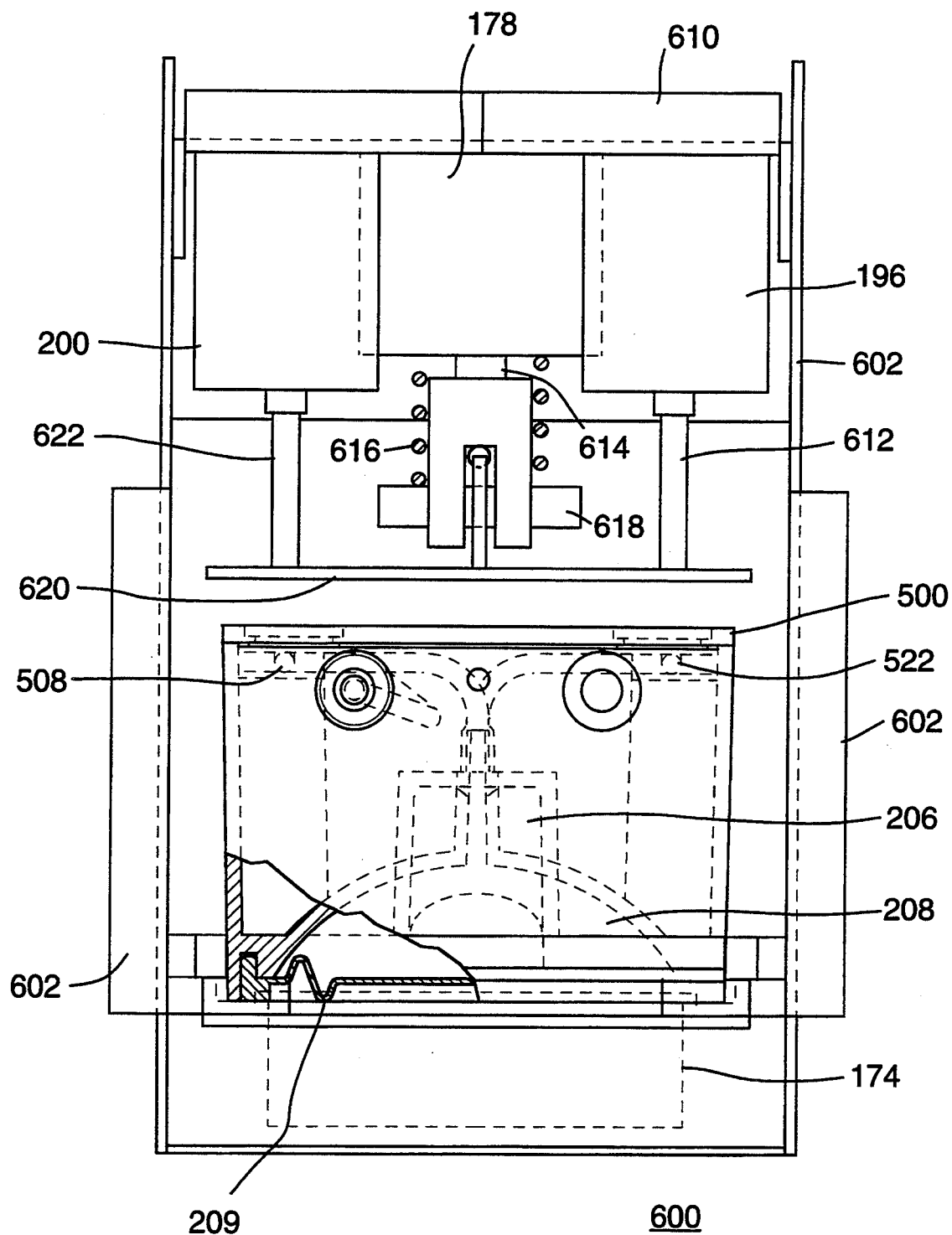
FIG. 15 is a front elevational view of the aspiration cassette of FIG. 6 as mounted in the aspiration cassette retaining mechanism of FIG. 12.
Figure 16:
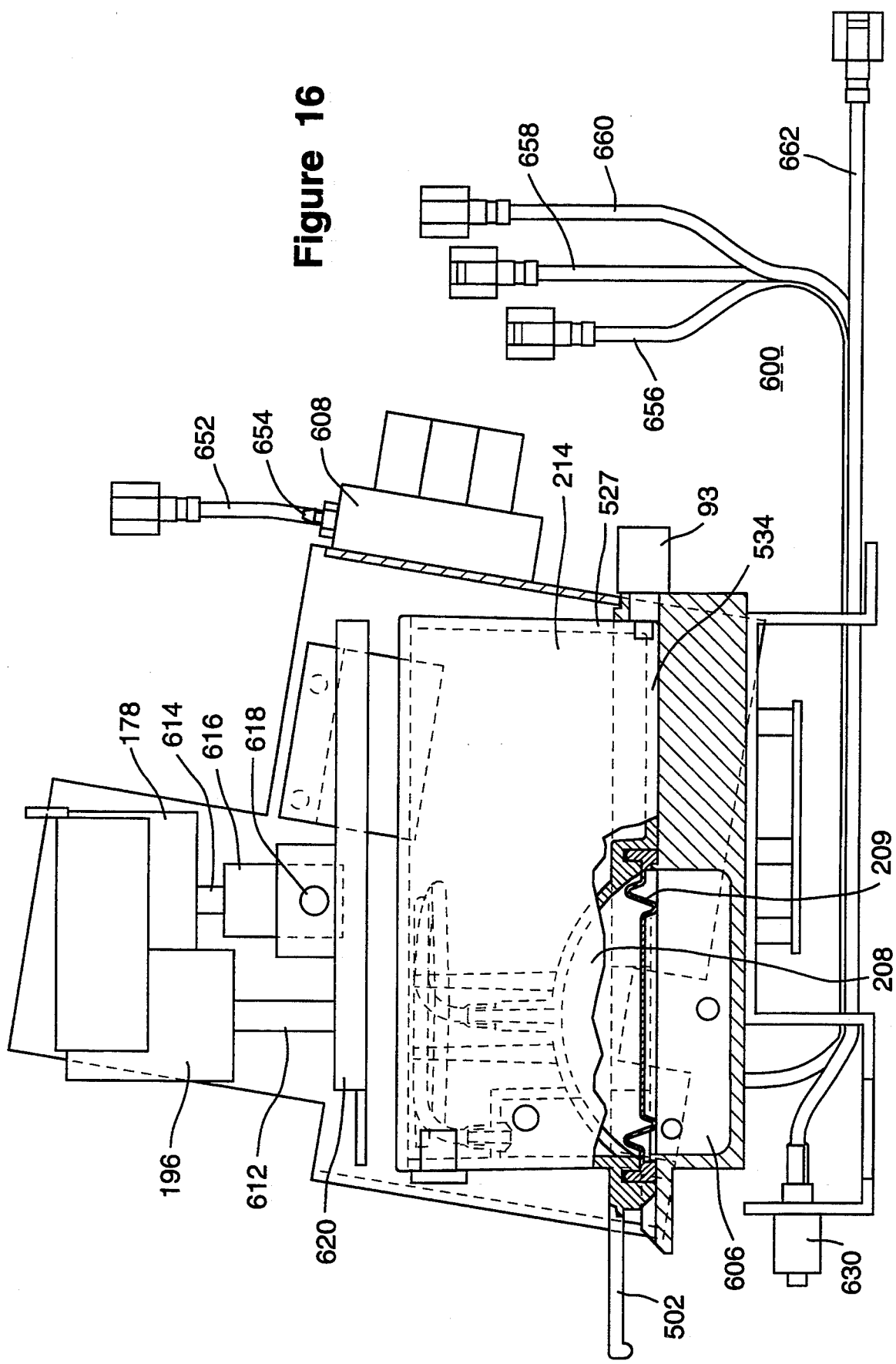
FIG. 16 is a side sectional view of the aspiration cassette of FIG. 6 as mounted in the aspiration cassette retaining mechanism of FIG. 13.

Referring now to FIGS. 14, 15 and 16 when an aspiration cassette 202 is inserted into the cassette receiving mechanism 600, the cassette sensor switch 93 is closed thereby causing the electronic control module 94 to activate the cylinder 178. When activated, the cylinder 178 exerts downward force on the clamp cylinder shaft 614. This force is transmitted and distributed by the clevis 616 to the dowel pin 618 and from the dowel pin to the clamp plate 620. The clamp plate 620 is thereby pushed against the top 500 of the aspiration cassette 202 to thereby seal diaphragm 209 against the chamber 174.

In order to remove the aspiration cassette 202 from the cassette retaining mechanism 600, the cylinder 178 is deenergized to thereby release the clamp plate 620 from the aspiration cassette 202. Referring now to FIG. 16 in further detail a tubing 652 is connected to an unregulated pneumatic supply having a pressure of approximately 45 psi. The tubing is connected to a barb fitting 654 which is mounted to the manifold 609. A tubing 656 is connected to an aspiration port, a tubing 658 is connected a vitrectomy luer connector, a tubing 660 is connected to a microscissors luer connector and a tubing 662 is connected to a pressurized gas luer connector for use in connection with fluid gas exchange.

Referring now to FIG. 17, there are shown eleven alternative embodiments of a gas pressure regulating arrangement which may be utilized in place of the first three-way valve 20 and the second three-way valve 36 of the gas delivery systems of FIGS. 1 and 2 and may also be utilized in place of electric/pressure regulator 98 pressure in the suction and pressure control system of FIG. 3.

Figures 17A, 17B:
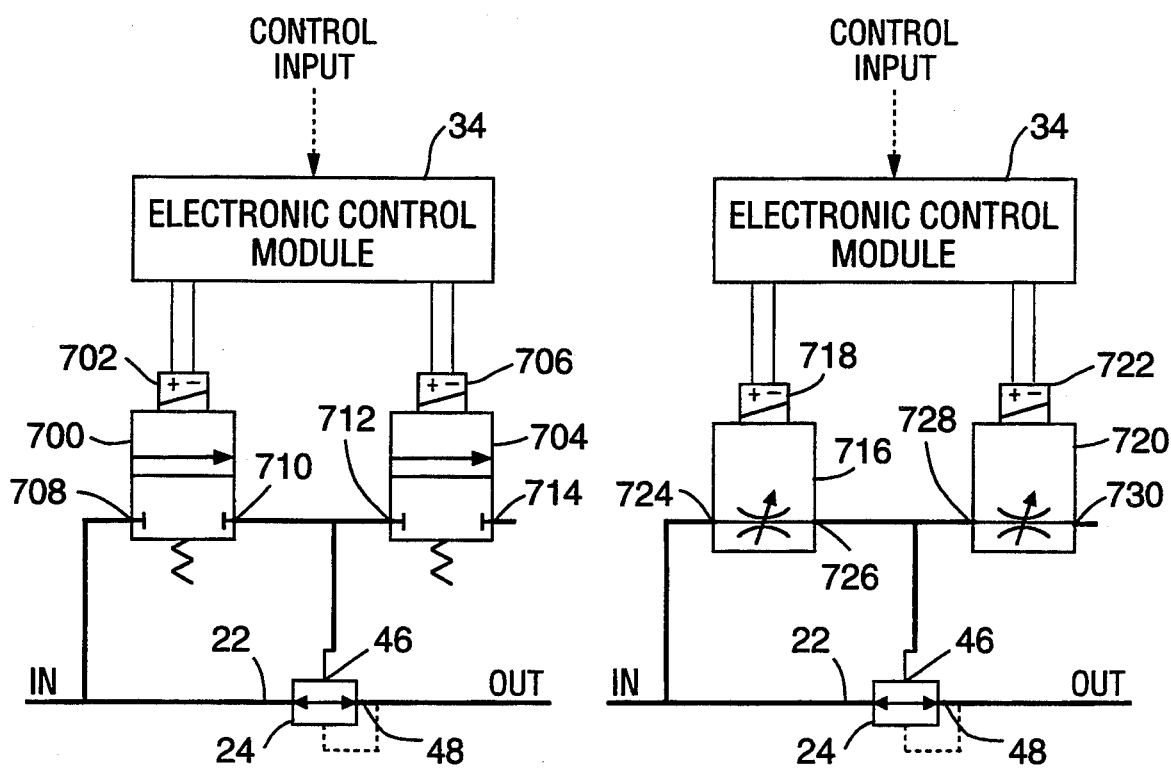
FIG. 17a is a first alternative embodiment of a pressure regulating arrangement which may be utilized in the gas delivery systems of FIGS. 1 and 2 and in the suction and pressure control system of FIG. 3.
FIG. 17b is a second alternative embodiment of a gas pressure regulating arrangement which may be utilized in the gas delivery systems of FIGS. 1 and 2 and in the suction and pressure control system of FIG. 3.

In particular, the arrangement of FIG. 17a includes a first two-way valve 700 having a solenoid 702 and a second two-way valve 704 having a solenoid 706. The input port 22 of the piloted regulator 24 is, as shown in FIGS. 1 and 2, connected to the output port 18 of the pump 14. A control signal which is related to pressure sensed by the pressure transducer 76 of the FIGS. 1 and 2 is provided to the electronic control module 34. Although it is possible to operate the arrangements shown in FIGS. 17a through 17i as well as the first three-way valve 20 and the second three-way valve 36 of FIGS. 1 and 2, without feedback from a pressure transducer (an open loop controller) the closed loop configuration of the preferred embodiment of the invention increases not only the precision but also the accuracy of gas pressure regulation.

In operation the solenoid 702 of the first three-way valve 700 is energized by the electronic control module 34 to thereby connect pressure from the output port 18 through a port 708 to a port 710 to the pilot chamber port 46 of the piloted pressure regulator 24. This increases the pressure at the pilot chamber port 46 thereby increasing the pressure at the output port 48. The second two-way valve 704 may be energized from the electronic control module 34 through the solenoid 706 to decrease the pressure at the pilot chamber port 46 to thereby decrease the pressure at the output port 48. When the second two-way valve 704 is energized the pilot chamber port 46 is vented through a port 712 to a port 714 which is vented to atmosphere. Both the first two-way valve 700 and the second two-way valve 704 may be left unenergized in order to maintain a constant pressure at the output port 48 of the piloted pressure regulator 24. The principal difficulty with this arrangement is that the first two-way valve 700 and the second two-way valve 704 do not instantaneously respond to electrical signals provided by the electronic control module 34. Thus, it is very difficult to avoid oscillation due to overshooting a target pressure.

Referring now to FIG. 17b there is shown a first proportional valve 716 which is connected to the electronic control module 34 through a solenoid 718. A second proportional valve 720 is connected to the electronic control module 34 through a solenoid 722. The first proportional valve 716 includes a port 724 and a port 726. The second proportional valve 720 includes a port 728 and a port 730. The embodiment shown in FIG. 17b operates in the same fashion as the embodiment of FIG. 17a, except that proportional valves are utilized to decrease the pressure applied to the pilot chamber valve 46 as a target pressure is approached. This arrangement avoids the overshoot problem and thereby avoids oscillation. The disadvantage with the use of proportional valves is higher cost for such valves and for additional electronic circuitry necessary to drive such valves in a proportional manner. Such electronic circuitry for control of proportional valves is well know in the art.

Figures 17C, 17D:
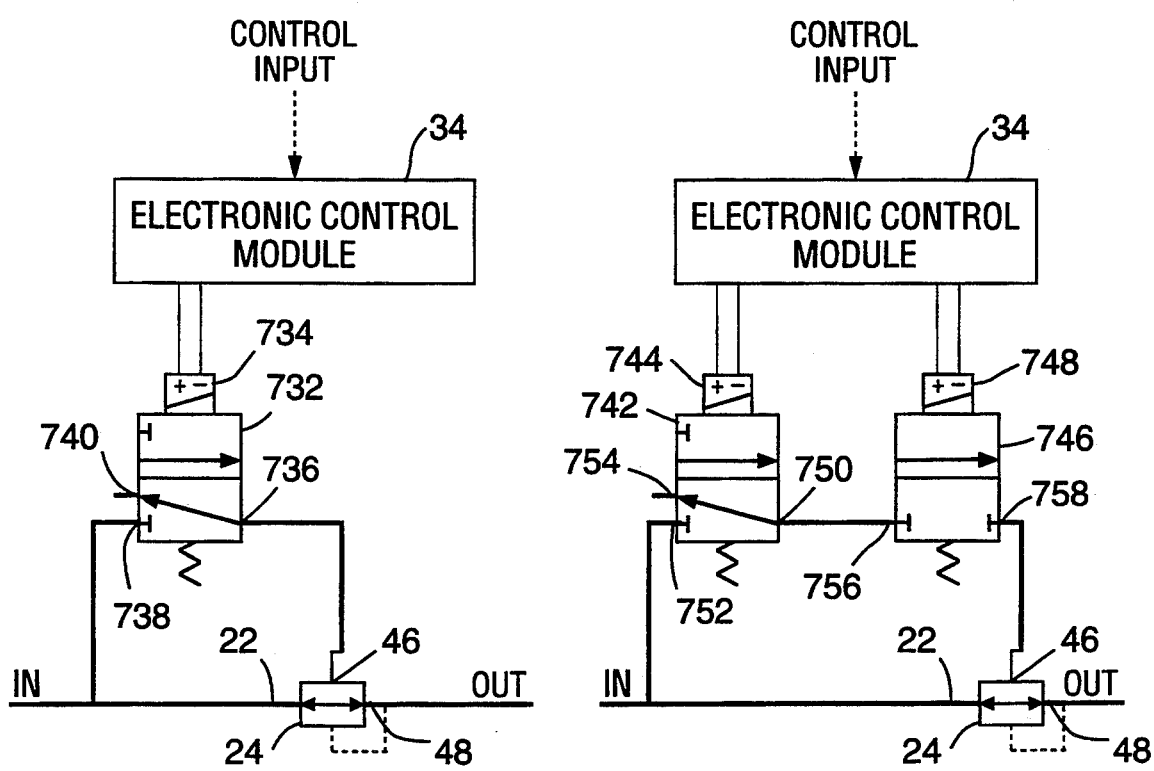
FIG. 17c is a third alternative embodiment of a gas pressure regulating arrangement which may be utilized in the gas delivery systems of FIGS. 1 and 2 and in the suction and pressure control system of FIG. 3.
FIG. 17d is a fourth alternative embodiment of a gas pressure regulating arrangement which may be utilized in the gas delivery systems of FIGS. 1 and 2 and in the suction and pressure control system of FIG. 3.

With reference to FIG. 17c a three-way valve 732 is connected to the electronic control module 34 through a solenoid 734. A port 736 is alternately connected between a port 738 and a port 740. In operation the electronic control module 34 energizes the solenoid 734 to thereby actuate the three-way valve 732. The actuated three-way valve 732 connects the pilot chamber port 46 to the output port 18 of the pump 14 as shown in FIGS. 1 and 2. Thus the pressure at the pilot chamber port 46 increases thereby increasing the pressure at the output port 48. To decrease the pressure at the output port 48 the solenoid 734 is de-energized to thereby cause the pilot chamber port 46 to be vented to atmosphere through the port 740. It is not possible to hold a constant pressure with the embodiment shown in FIG. 17c, but rather the pressure constantly oscillates about a target pressure. The life of the three-way valve 732 will, in this embodiment, be much shorter than in the arrangement shown in FIG. 17a in which a relatively constant pressure can be held.

Referring now to FIG. 17d, a three-way valve 742 is connected to the electronic control module 34 through a solenoid 744. A two-way valve 746 is connected to the electronic control module 34 through a solenoid 748. A port 750 of the three-way valve 742 is alternately connected to a port 752 and a port 754 and is also connected to a port 756 of the two-way valve 746. A port 758 of the two-way valve 746 is connected to the pilot chamber port 46 of the piloted pressure regulator 24. This arrangement is similar to that of FIG. 17c except that the two-way valve 746 has been added to hold a constant pressure. To increase pressure at the pilot chamber port 46 and thus at the output port 48, both the three-way valve 742 and the two-way valve 746 are actuated through the solenoids 744 and 748 respectively. To decrease pressure at the output port 48 of the piloted pressure regulator 24, the three-way valve 742 is de-energized through the solenoid 744 and the two-way valve 746 is energized through the solenoid 748, thereby allowing pressure at the pilot chamber port 46 to be vented to atmosphere. To hold a constant at the output port 48 of the piloted pressure regulator 24, the two-way valve 746 is de-energized. The operation of this embodiment is basically equivalent to that of FIG. 17a in that the same overshoot difficulties occur.

Figure 17E:
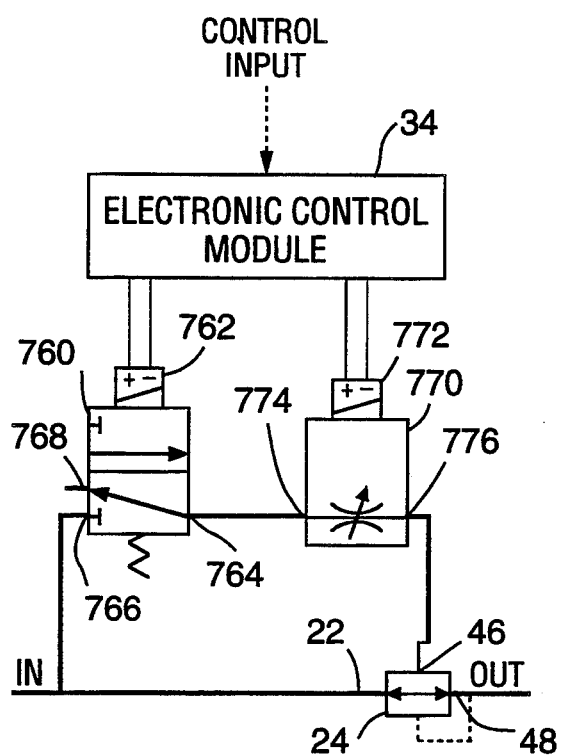
FIG. 17e is a fifth alternative embodiment of a gas pressure regulating arrangement which may be utilized in the gas delivery systems of FIGS. 1 and 2 and in the suction and pressure control system of FIG. 3.

With reference to FIG. 17e, a three-way valve 760 is connected to the electronic control module 34 through a solenoid 762. A port 764 of the three-way valve 760 alternately selects between a port 766 and a port 768. A proportional valve 770 is connected to the electronic control module 34 through a solenoid 772. A port 774 of the proportional valve 770 is connected to the port 764. A port 776 of the proportional valve 770 is connected to the pilot chamber port 46 of the piloted pressure regulator 24.

The operation of the embodiment shown in FIG. 17e is equivalent to the operation of the embodiment shown in FIG. 17b but has the advantage of requiring only one expensive proportional valve. To increase pressure at the output port 48 of the piloted pressure regulator 24, the three-way valve 760 is energized through the solenoid 762, and proportional valve 770 is energized through the solenoid 772 in proportion to the difference between the target pressure and the actual pressure. To decreased pressure, the three-way valve 760 is deenergized and the proportional valve 770 is energized in proportion to the difference between the actual pressure and the target pressure. Thus, the three-way valve 760 alternately connects the port 774 to the pump output 18 or to atmospheric pressure depending upon whether an increase or decrease in pressure is desired.

Figure 17F:
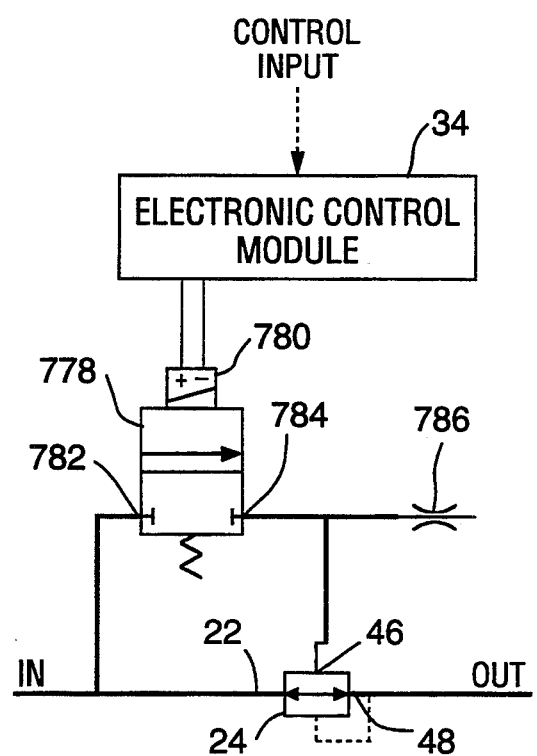
FIG. 17f is a sixth alternative embodiment of a gas pressure regulating arrangement which may be utilized in the gas delivery systems of FIGS. 1 and 2 and in the suction and pressure control system of FIG. 3.

Referring now to FIG. 17f, a two-way valve 778 is connected to the electronic control module 34 through a solenoid 780. A port 782 of the two-way valve 778 is connected to the pump output port 18 of FIG. 1. A port 784 is connected to both an orifice 786 and to the pilot chamber port 46 of the piloted pressure regulator 24. In operation the valve 778 is energized through the solenoid 780 to increase the pressure at the pilot port 46 and is de-energized to decrease the pressure at the pilot chamber port 46. The pressure at the pilot chamber port 46 and thus the output port 48 of the piloted pressure regulator 24 constantly oscillates about the target pressure. Therefore the life of the two-way valve 778 is relatively short.

Figure 17G:
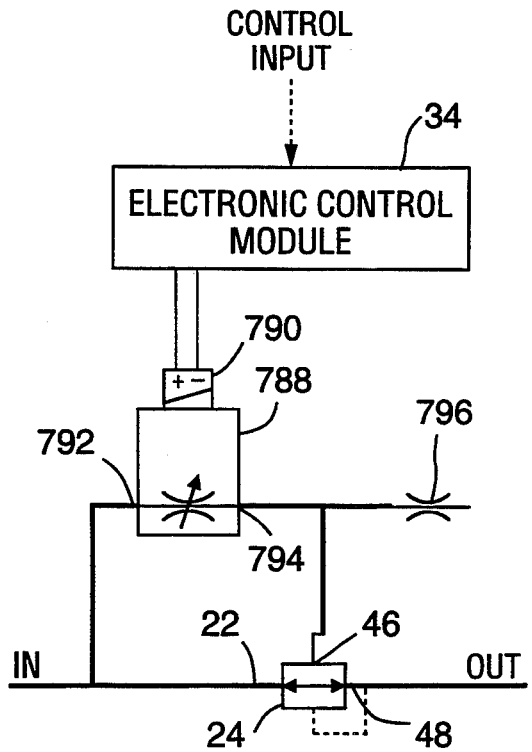
FIG. 17g is a seventh alternative embodiment of a gas pressure regulating arrangement which may be utilized in the gas delivery systems of FIGS. 1 and 2 and in the suction and pressure control system of FIG. 3.

Referring now to FIG. 17g, a proportional valve 788 is connected to the electronic control module 34 through a solenoid 790. A port 792 of the proportional valve 788 is connected the pump output port 18 of the FIGS. 1 and 2. A port 794 of the proportional valve 788 is connected to both an orifice 796 and the pilot chamber port 46 of the piloted pressure regulator 24. The embodiment of FIG. 17g is similar to that of FIG. 17f except that the more expensive proportional valve 788 is utilized in place of the two-way valve 778. A constant pressure can be held at the pilot chamber port 46 by holding constant the opening of the proportional valve 788. The valve of the proportional valve 788 is opened to increase pressure and is decreased to decrease pressure provided to the pilot chamber port 46 of the piloted pressure regulator 24.

Figure 17H:
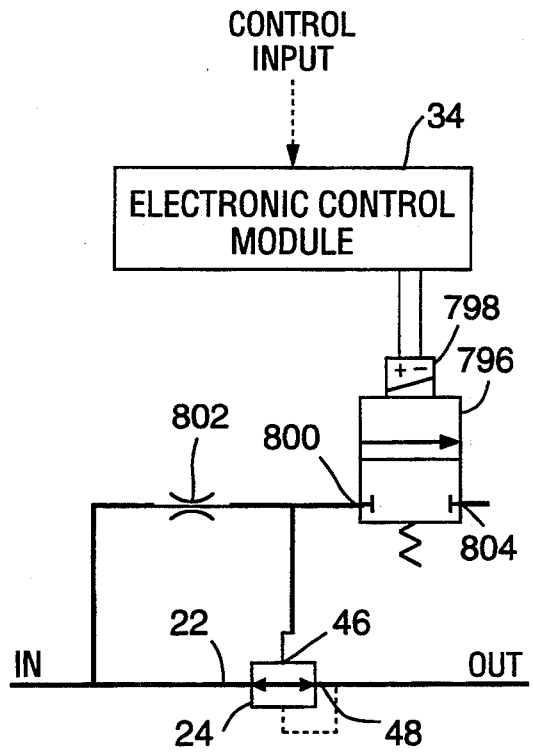
FIG. 17h is an eighth alternative embodiment of a gas pressure regulating arrangement which may be utilized in the gas delivery systems of FIGS. 1 and 2 and in the suction and pressure control system of FIG. 3.

With reference to FIG. 17h, a two-way valve 796 is connected to the electronic control module 34 through a solenoid 798. A port 800 of the two-way valve 796 is connected to both an orifice 802 and the pilot chamber port 46 of the piloted pressure regulator 24. The other side of the orifice 802 is connected to the pump output port 18 as shown in FIGS. 1 and 2. A port 804 of the two-way valve 796 is vented to atmosphere. In operation, the two-way valve 796 is de-energized to increase the pressure at the pilot chamber port 46 and is energized to decrease the pressure at the pilot chamber port 46. Thus, the pressure at the pilot chamber port 46 and consequently the pressure at the output port 48 of the piloted pressure regulator 24 constantly oscillates about the target pressure. As a result, the life of the valve 796 is relatively short. In further detail, when the valve 796 is de-energized, pressure from the pump output 18 is provided to the pilot chamber port 46 through the orifice 802. When the valve 796 is energized, the pressure at the port 46 is vented to atmosphere through the port 804.

Figure 17I:
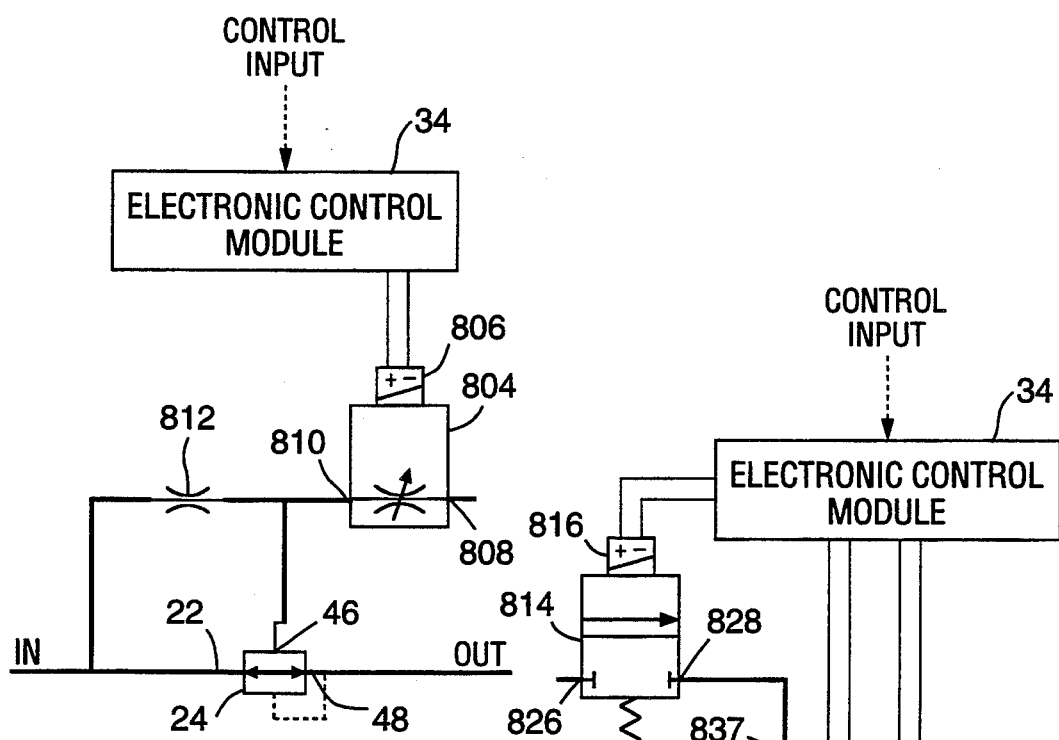
FIG. 17i is a ninth embodiment of a gas pressure regulating arrangement which may be utilized in the gas delivery systems of FIGS. 1 and 2 and in the suction and pressure control system of FIG. 3.

With reference to FIG. 17i a proportional valve 804 is connected to the electronic control module 34 through a solenoid 806. A port 808 of the proportional valve 804 is vented to atmosphere, while a port 810 of the proportional valve 804 is connected to both the pilot chamber port 46 of the piloted pressure regulator 24 and to an orifice 812. The other side of the orifice is connected to the pump output port 18 of the FIGS. 1 and 2. The embodiment shown in FIG. 17i is similar to that shown in FIG. 17h except that a more expensive proportional valve 804 is used. A constant pressure can be held by holding constant the opening of the proportional valve 804. The opening of the proportional valve 804 is decreased to increase pressure provided to the pilot chamber port 46 and is increased to decrease pressure provided to the pilot chamber port 46. Stated another way, as the proportional valve 804 opens, pressure is vented to atmosphere to thereby lower the pressure provided to the pilot chamber port 46. This arrangement is used in certain commercially available electrically controlled pressure regulators, notably the Fairchild Model T6000. However, the Fairchild Model T6000 in no way employs any type of closed loop arrangement to more accurately and precisely control the pressure at the output port 48 of the piloted pressure regulator 24. One disadvantage of the embodiments of FIGS. 17f through 17i is that they constantly bleed gas from the pump 14 to atmosphere. This is a concern if the gas used is expensive, toxic or in limited supply.

Figure 17J:
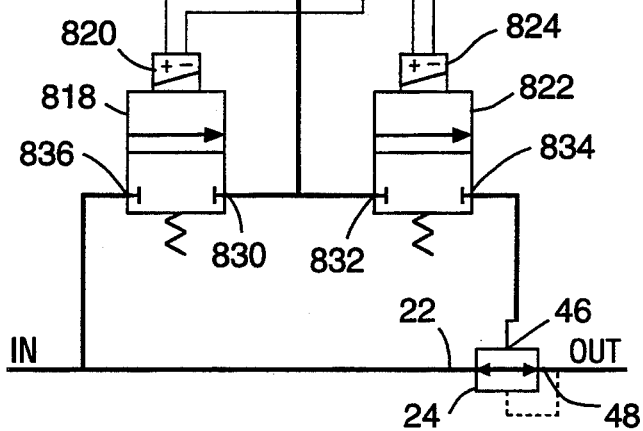
FIG. 17j is a tenth alternative embodiment of a gas pressure regulating arrangement which may be utilized in the gas delivery system of FIGS. 1 and 2 in the gas delivery systems of FIGS. 1 and 2 and in the suction and pressure control system of FIG. 3.

Referring now to FIG. 17j, a first two-way valve 814 is connected to the electronic control module 34 through a solenoid 816. A second two-way valve 818 is connected to the electronic control module 34 through a solenoid 820. A third two-way valve 822 is connected to the electronic control module 34 through a solenoid 824. A port 826 of the first two-way valve 814 is vented to atmosphere. A port 828 of the first two-way valve is connected to both a port 830 of the second two-way valve 818 and a port 832 of the third two-way valve 822. A port 834 of the third two-way valve 822 is connected to the pilot chamber port 46 of the piloted pressure regulator 24. A port 836 is connected to both the pump output 18 of FIGS. 1 and 2 and to the port 22 of the piloted pressure regulator 24.

In operation, the embodiment shown in FIG. 17j solves the overshoot problem without resorting to an expensive proportional valve. An increase in pressure at the output port 48 of the piloted pressure regulator 24 is accomplished in 4 steps. First the second two-way valve 818 is energized and the first two-way valve 814 and the third two-way valve 822 are de-energized. This charges a conduit 837 (which joins all three valves) to the pressure of the pump output port 18. Second, the second two-way valve 818 is de-energized sealing off the conduit 837. Third, the third two-way valve 822 is energized thereby connecting the conduit 837 to the pilot chamber port 46 of the piloted pressure regulator 24. Since the conduit 837 was originally charged to a pressure higher than that at the pilot chamber port 46, the pressure in both after equilibration will be somewhat greater than the original pressure at the pilot chamber port 46 of the piloted pressure regulator 24. Finally, the third two-way valve 822 is de-energized sealing off the pilot chamber and readying the system to start another cycle.

A decrease in pressure at the output port 48 of the piloted pressure regulator 24 is accomplished is similar fashion, except that it is the first two-way valve 814 which is initially energized in order to vent the conduit 836 to atmospheric pressure. If the volume and initial pressure of the conduit 836 are respectively $V_{conduit}$ and $P_{conduit}$, and the volume and initial pressure of the pilot chamber of the piloted pressure regulator 24 are respectively $V_{chamber}$ and $P_{chamber}$ then the final pressure (assuming no significant temperature change) is given by $P_{chamber}+(P_{conduit}-P_{chamber})\times(V_{conduit}/(V_{conduit}+V_{chamber}))$. Thus, the change in pressure is precisely defined by the volume of the conduit 836 and the volume of the pilot chamber of the piloted pressure regulator 24 and is independent of the delays in valve opening and closing which cause overshoot in some of the other configurations.

Figure 17K:
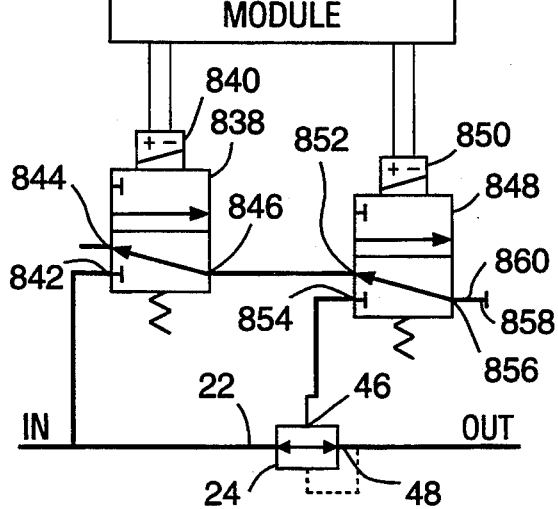
FIG. 17k is an eleventh embodiment of a gas pressure regulating arrangement which may be utilized in the gas delivery system of FIGS. 1 and 2 in the gas delivery systems of FIGS. 1 and 2 and in the suction and pressure control system of FIG. 3.

With reference now to FIG. 17k, a first three-way valve 838 is connected to the electronic control module through a solenoid 840. A port 842 of the first three-way valve 838 is connected to the pump output 18 of FIGS. 1 and 2 and to the port 22 of the piloted pressure regulator 48. A port 844 of the first three-way valve 838 is vented to atmosphere. A port 846 of the three-way valve 838 alternately selects between the port 842 and the port 844. A second three-way valve 848 is connected to the electronic control module 34 through the solenoid 850. A port 852 of the second three-way valve 848 is connected to the port 846. A port 854 of the second three-way valve 848 is connected to the pilot chamber port 46 of the piloted pressure regulator 24. A port 856, which port alternately selects between the ports 852 and 854 in connected to a plug 858.

In operation, the embodiment shown in FIG. 17k is similar to the embodiment shown in FIG. 17j, but only requires two valves instead of three. To increase the pressure at the output port 48 of the piloted pressure regulator 24, the second three-way valve 848 is initially de-energized and the first three-way valve 838 is energized to connect the second three-way valve 848 to the pump output port 18 of FIGS. 1 and 2. This charges a conduit 860, which ends at the plug 858, to the pressure of the pump output 18. (This conduit 860 includes the internal passages of the second three-way valve 848 which communicate with the conduit, so that even if a plug is directly at the port 856, the internal passages of the three-way valve 848 provide a finite volume). The second three-way valve 848 is then energized, simultaneously sealing off the conduit 860 from the pump output 18 and connecting the conduit 860 to the pilot chamber port 46. The pressures in the pilot chamber of the piloted pressure regulator 24 and in the conduit 860 then equilibrate to a new pressure in accordance with the same formula given for FIG. 17j. To decrease the pressure at the pilot chamber port 46 and thus at the output 48, the first three-way valve 838 is de-energized to connect the second three-way valve 848 to atmospheric pressure through the port 844, and the second three-way valve 848 is cycled.

The preferred embodiment of the gas delivery system 10 of FIG. 1 and the gas delivery system 82 of FIG. 2 each employ the arrangement of FIG. 17k, because the arrangement is relatively low in cost, is not prone to overshoot and does not consume gas except during changes in the target or desired pressure. The arrangement of FIG. 17k is well-suited for a gas delivery system because the target pressure is changed only infrequently. Valve noise and wear which are the main drawbacks of this arrangement occur only during changes in pressure. As shown in FIGS. 1 and 2, a muffler 30 is utilized to reduce valve noise resulting from the release of pressure to atmosphere.

For suction and pressure control however, target or desired pressure changes continuously. For such applications, an arrangement employing a proportional valve is preferred, despite the higher cost. As described previously, an electronically controlled pressure regulator comprising all of the elements of FIG. 17i is commercially available, and is utilized in the preferred embodiment of the suction and pressure system 90.

Figure 18:
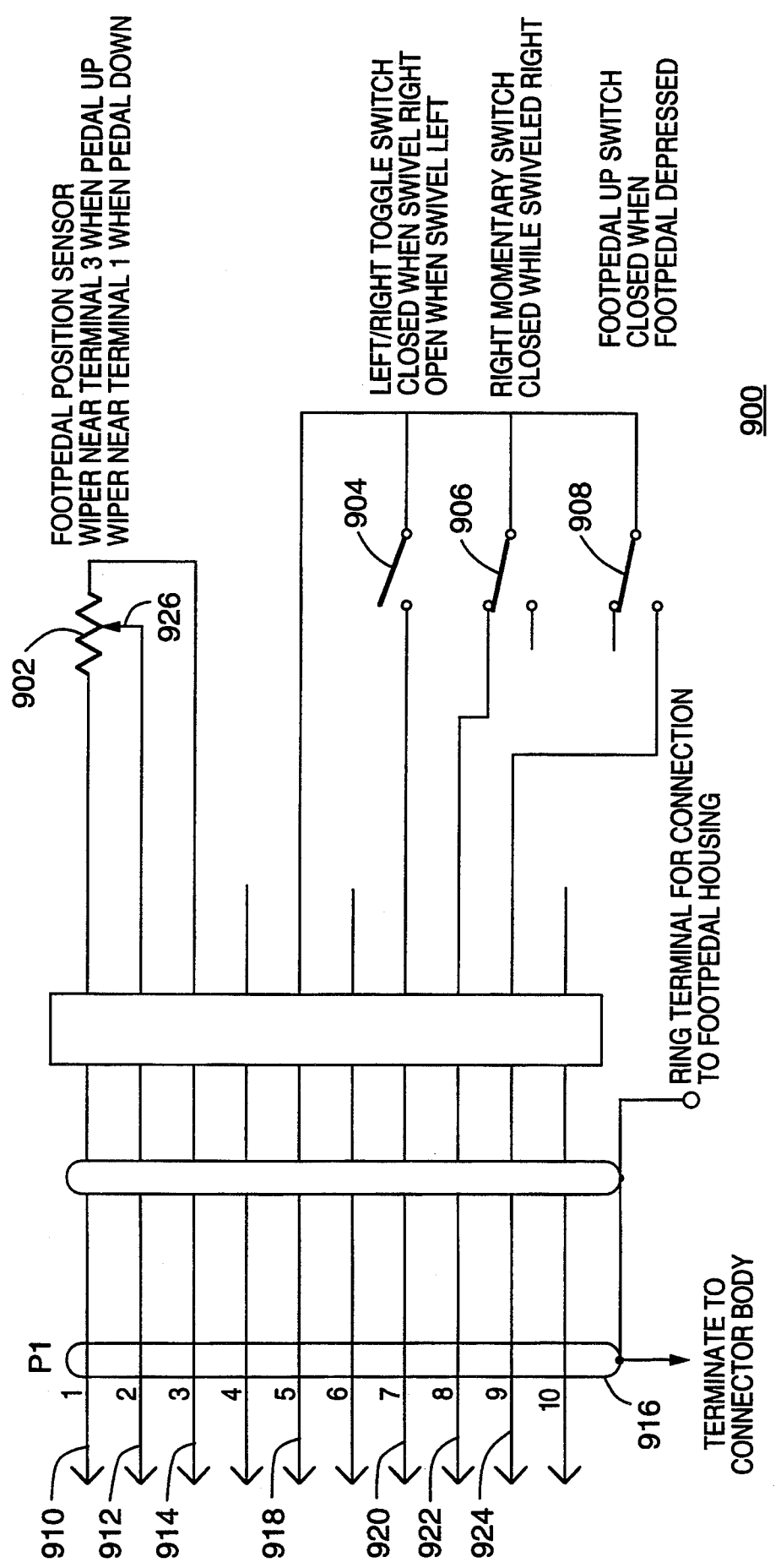
FIG. 18 is a schematic diagram of a footpedal controller of the present invention.

Referring now to FIG. 18 a footpedal controller 900 of the present invention is disclosed. The footpedal controller 900 may be utilized as the footpedal controller 97 of FIGS. 3 and 5. The footpedal controller 900 consists of a rheostat 902, a single pole single throw switch 904, a first double pole single throw switch 906 and a second double pole single throw switch 908. The rheostat 902 is connected to the terminals 910, 912 and 914 of a ten-pin plug 916. The switches 904, 906 and 908 each have one side connected to a common terminal 918. The switch 904 has its remaining terminal connected to a terminal 920. The switch 906 has its remaining terminal connected to a terminal 922, and the switch 908 has its remaining terminal connected to a terminal 924 of the ten pin plug 916.

In operation when the footpedal controller 900 has its pedal up a wiper 926 of the rheostat 902 positioned closer to end of the rheostat 902 which is connected to terminal 910. When the footpedal controller has its pedal down, the wiper 926 is closer to the end of the rheostat which is connected to the terminal 914.

The switch 904 is a left/right toggle switch and is closed when swiveled right and is open with swiveled left. The switch 906 is a momentary switch which is closed while swiveled right. The switch 908 simply senses when the footpedal controller 900 is depressed.

Figure 19:
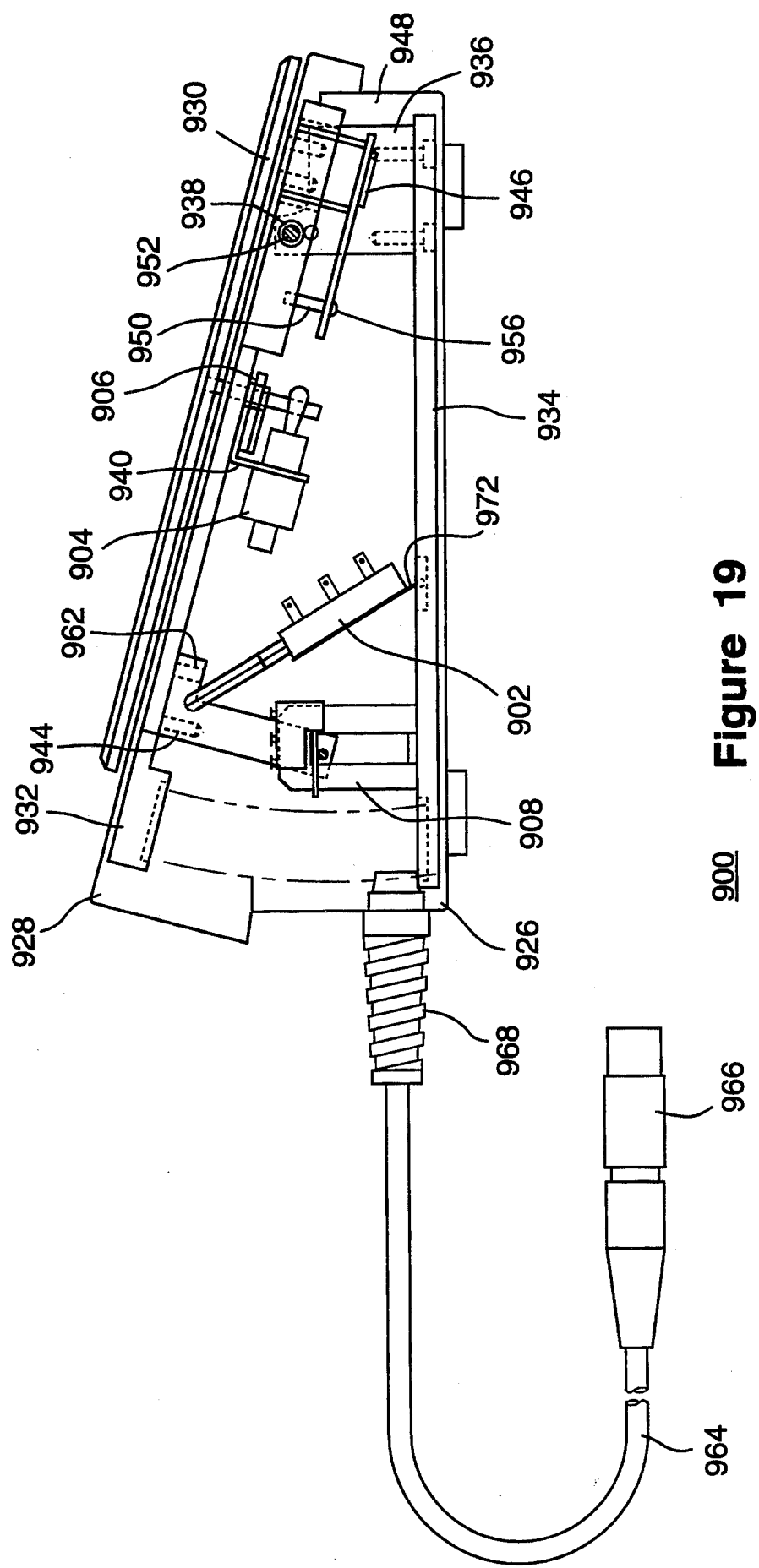
FIG. 19 is a side sectional view of the footpedal controller of FIG. 18.

Referring now to FIG. 19, the mechanical features of the footpedal controller 900 are shown. The footpedal controller 900 includes a bottom pan 926, a top pan 928, a swivel plate 930, a plate treadle 932, a plate base 934, a treadle shaft support 936, a treadle shaft bearing 938, and a toggle switch bracket 940. The footpedal controller 900 further includes an up-switch bracket 942, a limit stop post 944, a swivel plate return lever 946, and swivel shaft bearing 948. The footpedal controller 900 additionally includes a spring post 950, a treadle shaft 952, a treadle return spring 954, a swivel return spring 956, and the microswitch 908. The footpedal controller 900 also includes the toggle switch 904, a swivel plate roller bearing 962 a ten conductor cable 964, a ten pin connector 966, a cable strain relief 968, and the linear position sensor (rheostat) 902. The footpedal controller also includes a bracket 972 and the momentary switch 906.

In operation when a surgeon's foot presses down upon the top of the footpedal controller 900 the force exerted adjusts the linear position sensor 902. The toggle switch 904 closes when the top of the footpedal controller 900 is swiveled to the right and opens when the top of the footpedal controller 900 is swiveled to the left. The microswitch 908 closes when the top of the footpedal controller is pressed down.

It is apparent from the foregoing that a new and improved system and methods have been provided for the control of vacuum and pressure for use with surgical procedures. While only certain preferred embodiments have been described in detail, as will be apparent to those familiar with the art, certain changes and/or modifications can be made without departing from the scope of the invention as defined by the following claims.

What is claimed is:

1. A container for aspirating fluids from a surgical site comprising:
   a first chamber having a flexible membrane, said flexible membrane operative to transmit pressure and vacuum to said first chamber;
   a second chamber having a volume larger than that of said first chamber, said second chamber selectively connected to said first chamber to allow the transfer of aspirated fluids from said first chamber to said second chamber when pressure is applied to said flexible membrane;
   a port operative to provide vacuum from said first chamber to a surgical instrument when vacuum is applied to said flexible membrane; and
   valve means operative to connect said first chamber to said port when vacuum is applied to said flexible membrane and to connect said first chamber to said second chamber when pressure is applied to said flexible membrane.

2. The container of claim 1 further comprising:
   a drip chamber connected between said first chamber and said port operative to provide a visual indication of fluid flow.

3. The container of claim 1 wherein said valve means comprises:
   a first pinch valve operative to isolate said first chamber from said second chamber when vacuum is applied to said flexible membrane; and
   a second pinch valve operation to prevent communication of pressure from said first chamber to said port.

4. The container of claim 1 wherein said second chamber further comprises a vent operative to maintain said second chamber at atmospheric pressure.

5. A container for aspirating fluids from a surgical site comprising:
   a first chamber;
   a second chamber having a volume larger than that of said first chamber;
   a first wall having disposed therein a first flexible grommet and a second flexible grommet;
   a second wall including a projection therefrom, said second wall substantially perpendicular to said first wall and said projection from said second wall adjacent to said first flexible grommet;
   a third wall including a projection therefrom, said third wall substantially perpendicular to and connected to said first wall and substantially parallel to said second wall, said projection from said third wall adjacent to said second flexible grommet;
   a first tubing connected between an aspiration port and said first chamber, said first tubing disposed in part across said projection from said second wall;
   a second tubing having a first end connected to said first chamber and having a second end disposed within said second chamber, said second tubing disposed in part across said projection from said third wall;
   a fourth wall having a bore communicating with said first chamber, said fourth wall substantially parallel to said first wall, substantially perpendicular to said second and third walls and connected thereto;

and a flexible membrane positioned across said bore, operative to communicate pressure and vacuum to said first chamber.

6. The container of claim 5 further comprising:

a fifth wall containing said aspiration port, said fifth wall substantially perpendicular to and connected to an edge of each of said first wall, said second wall, said third wall and said fourth wall.

7. The container of claim 6 further comprising:

a handle attached to said fifth wall, said handle substantially perpendicular to said fifth wall and substantially parallel to said fourth wall.

* * * * *